United States Patent
Nakamura et al.

(10) Patent No.: US 12,385,019 B2
(45) Date of Patent: Aug. 12, 2025

(54) BUCKWHEAT-DERIVED C-GLYCOSYLTRANSFERASE GENE AND UTILIZATION THEREOF

(71) Applicant: Suntory Holdings Limited, Osaka (JP)

(72) Inventors: Noriko Nakamura, Kyoto (JP); Naoko Okitsu, Osaka (JP); Yukihisa Katsumoto, Kyoto (JP)

(73) Assignee: SUNTORY HOLDINGS LIMITED, Tokyo (JP)

( * ) Notice: Subject to any disclaimer, the term of this patent is extended or adjusted under 35 U.S.C. 154(b) by 69 days.

(21) Appl. No.: 17/765,692

(22) PCT Filed: Sep. 25, 2020

(86) PCT No.: PCT/JP2020/036451
§ 371 (c)(1),
(2) Date: Mar. 31, 2022

(87) PCT Pub. No.: WO2021/065749
PCT Pub. Date: Apr. 8, 2021

(65) Prior Publication Data
US 2023/0220357 A1 Jul. 13, 2023

(30) Foreign Application Priority Data
Oct. 1, 2019 (JP) .................. 2019-181693

(51) Int. Cl.
| | |
|---|---|
| *A01H 5/02* | (2018.01) |
| *A01H 6/74* | (2018.01) |
| *C12N 9/02* | (2006.01) |
| *C12N 9/10* | (2006.01) |
| *C12N 9/88* | (2006.01) |
| *C12N 15/82* | (2006.01) |

(52) U.S. Cl.
CPC ............. *C12N 9/1051* (2013.01); *A01H 5/02* (2013.01); *A01H 6/749* (2018.05); *C12N 9/0071* (2013.01); *C12N 9/1007* (2013.01); *C12N 9/88* (2013.01); *C12N 15/825* (2013.01); *C12Y 114/14* (2013.01); *C12Y 201/01* (2013.01); *C12Y 204/01* (2013.01); *C12Y 402/01105* (2013.01)

(58) Field of Classification Search
None
See application file for complete search history.

(56) References Cited

U.S. PATENT DOCUMENTS

2020/0283782 A1   9/2020   Nakamura et al.

FOREIGN PATENT DOCUMENTS

WO    2019/069946 A1    4/2019

OTHER PUBLICATIONS

GenBank: AB909376, 2014, https://www.ncbi.nlm.nih.gov/nuccore/7AB909376.*
GenBank: AB909375, 2014, https://www.ncbi.nlm.nih.gov/nuccore/AB909375.1.*
GenBank Accession: AB909375.1 https://www.ncbi.nlm.nih.gov/nuccore/AB909375; Available: Nov. 18, 2014 (Year: 2014).*
GenBank Accession: X77943; https://www.ncbi.nlm.nih.gov/nuccore/X77943; Available Nov. 14, 2006 (Year: 2006).*
Chen et al., ACS Catalysis 8.6 (2018): 4917-4927. (Year: 2018).*
Poulos et al., Cytochrome P450: structure, mechanism, and biochemistry (2015): 3-32. (Year: 2015).*
Nagatomo et al., The Plant Journal 80.3 (2014): 437-448. (Year: 2014).*
Yabuya, et al., Euphytica 98 (1997): 163-167. (Year: 1997).*
Jiang et al., Plants 5.2 (2016): 27. (Year: 2016).*
Tanaka et al., Fifty years of cytochrome P450 research (2014): 207-229. (Year: 2014).*
Sugio et al., Journal of bioscience and bioengineering 105.3 (2008): 300-302. (Year: 2008).*
Chandler et al., Biotechnology letters 33.2 (2011): 207-214. (Year: 2011).*
Liu et al., Plant Cell 32.9 (2020): 2917-2931. (Year: 2020).*
Guo et al., 2004, Proc. Natl. Acad. Sci. USA 101: 9205-9210. (Year: 2004).*
Katsumoto et al., Plant and cell physiology 48.11 (2007): 1589-1600 (Year: 2007).*
Akashi et al., Plant Physiology 137.3 (2005): 882-891 (Year: 2005).*
Rauter et al., "C-Glycosylflavonoids: Identification, Bioactivity and Synthesis", Natural Product Communications, Jan. 1, 2007, vol. 2, No. 11, pp. 1175-1196, cited in EP Search Report dated Jan. 3, 2024. (22 pages).
Nagatomo, Y. et al., "Purification, molecular cloning and functional characterization of flavonoid C-glucosyltransferases from *Fagopyrum esculentum* M. (buckwheat) cotyledon", The Plant Journal, 2014, vol. 80, pp. 437-448; Cited in ISR. (12 pages).
International Search Report dated Nov. 24, 2020, issued in counterpart Application No. PCT/JP2020/036451. (3 pages).
*Arabidopsis thaliana* ortholog of sugar beet HS1 PRO-12 (HSPRO2), mRNA, NCBI Reference Sequence: NM 129558.3. (3 pages); cited in CN Office Action dated Jul. 8, 2024.

* cited by examiner

*Primary Examiner* — Jason Deveau Rosen
(74) *Attorney, Agent, or Firm* — WHDA, LLP

(57) ABSTRACT

Transgenic plants with blue flower color, or their inbred or outbred progeny, or their propagules, partial plant bodies, tissues or cells, are provided. A buckwheat-derived C-glucosyltransferase (CGT) gene or its homolog is transferred into a host plant to cause delphinidin-type anthocyanins and flavone mono-C-glycosides to be copresent in the plant cells.

11 Claims, 6 Drawing Sheets
Specification includes a Sequence Listing.

BUCKWHEAT-DERIVED C-GLYCOSYLTRANSFERASE GENE AND UTILIZATION THEREOF

FIELD

The present invention relates to buckwheat-derived C-glucosyltransferase (CGT) genes or their homologs, and to a method for creating transgenic plants with blue flower color, comprising a step of using the genes to cause delphinidin-type anthocyanins and flavone mono-C-glycosides to be copresent in plant cells.

BACKGROUND

Rose, chrysanthemum and carnation are industrially important ornamental flowers worldwide. Rose in particular, being the most popular flowering plant, has a record of cultivation since ancient times, and it has been artificially crossbred for hundreds of years. One problem, however, has been that none of the hybridizable related species have wild varieties with blue flower color, and it has therefore been difficult to create rose varieties with blue flower color by conventional cross-breeding and mutation breeding. Creating completely new blue flower colors should lead to new demand for even wider uses of ornamental flowers, and should help to increase production and consumption. It has therefore been attempted to create roses with blue flower colors by genetic engineering methods.

Flowers with purple to blue colors, for example, are known to abundantly contain delphinidin-type anthocyanins having delphinidin, petunidin and malvidin backbones, but since ornamental flowers such as rose cannot produce such delphinidin-type anthocyanins, research continues to be conducted with the aim of artificially producing delphinidins by expressing the flavonoid 3',5'-hydroxylase gene that is necessary for their synthesis (NPL 1). However, even when plant metabolism is artificially modified in order to express an enzyme gene that produces a substance of interest in the recombinant plant, often little or absolutely none of the substance of interest accumulates.

Moreover, the color of a flower changes not only by the structures of the anthocyanins themselves as the essential pigments, but also due to copresent flavonoids (also known as copigments), metal ions, and the vacuole pH. Flavones or flavonols are typical copigments that form sandwich-like layers with anthocyanins and render the anthocyanins blue, producing a deepening effect (NPL 2). This is known as the "copigment effect". Flavones, in particular, are known to exhibit a powerful copigment effect, and analysis of gene recombinant carnations, for example, has demonstrated that flavones exhibit a significant copigment effect (NPL 3). For Dutch iris, it has been reported that a higher ratio of the total flavone content with respect to the total delphinidin content results in a more powerful copigment effect, and a bluer color (NPL 4).

However, not all plants can produce flavones, and it is known that roses and petunias do not store flavones. Attempts have therefore been made to modify flower color by expressing in the plants different genes coding for proteins having activity for synthesizing flavones from flavanones (PTL 1).

In plants, flavones are distributed not only in free form but also as glycosides, with flavone O-glycosides and flavone C-glycosides being formed primarily, and flavone C-glycosides being known to exhibit a particularly powerful copigment effect. For example, isovitexin, as one type of flavone C-glycoside, has been reported to exhibit a copigment effect with anthocyanins in Japanese garden iris (*Iris ensata* Thunb.), and to produce a blue flower color via stabilization of anthocyanins (NPL 5). One known biosynthetic pathway for flavone C-glycosides is synthesis from flavanones via reaction catalyzed by flavanone 2-hydroxylase (F2H), C-glucosyltransferase (CGT) and dehydratase (FDH) (NPL 6).

Previously it has been reported that roses with blue flower color were created by introducing the *Campanula*-derived F3',5'H gene and the torenia-derived MT gene, licorice-derived F2H gene, rice-derived CGT gene and *Lotus japonicus*-derived FDH gene, to cause copresence of delphinidin-type anthocyanins and flavone C-glycosides in plant cells (PTL 2). However, the flower colors of rose varieties created in this manner are found to have a strong reddish tint, and it is therefore still desired to develop techniques for controlling blue color expression in order to allow uniform and stable creation of roses with bluer flower colors.

CITATION LIST

Patent Literature

[PTL 1] Japanese Unexamined Patent Publication No. 2000-279182
[PTL 2] International Patent Publication No. 2019/069946
[PTL 3] International Patent Publication No. 2008/156206

Non Patent Literature

[NPL 1] Phytochemistry Reviews 5, 283-291
[NPL 2] Prog. Chem. Org. Natl. Prod. 52
[NPL 3] Phytochemistry, 63, 15-23(2003)
[NPL 4] Plant Physiol. Bioch. 72, 116-124(2013)
[NPL 5] Euphytica 115, 1-5(2000)
[NPL 6] FEBS Lett. 589, 182-187(2015)

SUMMARY

Technical Problem

The problem to be solved by the invention is to create a transgenic plant having a uniform and stable blue flower color (RHS Color Chart 5th Edition: Violet-Blue group/Blue group and/or hue angle: 339.7°-270.0°), based on research on the causes of redness in flower color.

Solution to Problem

As a result of ardent research and much experimentation on this problem, the present inventors have found that flavone di-C-glycosides are a cause of redness, and that the copigment effect of flavone mono-C-glycosides with delphinidin-type anthocyanins is significantly higher than that of flavone di-C-glycosides. By transferring the buckwheat-derived CGT gene, which was selected from among various CGT genes, the present inventors further succeeded in significantly accumulating only flavone mono-C-glycosides in plant petals. The invention has been completed upon these findings.

Specifically, the present invention provides the following.
[1] A buckwheat-derived CGT gene or its homolog, wherein:
the buckwheat-derived CGT gene or its homolog is selected from the group consisting of:

(1-a) a polynucleotide consisting of the nucleotide sequence listed as SEQ ID NO: 11;

(1-b) a polynucleotide that hybridizes with a polynucleotide consisting of the nucleotide sequence complementary to the nucleotide sequence listed as SEQ ID NO: 11, under stringent conditions, and has the same activity as the polynucleotide of (1-a); and (1-c) a polynucleotide that encodes a protein consisting of the amino acid sequence listed as SEQ ID NO: 12.

[2] The buckwheat-derived CGT gene or its homolog according to [1], to which the *Arabidopsis thaliana* ADH gene-derived untranslated region (5'-UTR) (SEQ ID NO: 15) or the *Arabidopsis thaliana* HSPRO gene-derived untranslated region (5'-UTR) (SEQ ID NO: 13) has been added.

[3] A vector comprising a buckwheat-derived CGT gene or its homolog, wherein the buckwheat-derived CGT gene or its homolog is selected from the group consisting of:

(1-a) a polynucleotide consisting of the nucleotide sequence listed as SEQ ID NO: 11;

(1-b) a polynucleotide that hybridizes with a polynucleotide consisting of the nucleotide sequence complementary to the nucleotide sequence listed as SEQ ID NO: 11 under stringent conditions and has the same activity as the polynucleotide of (1-a);

(1-c) a polynucleotide that encodes a protein consisting of the amino acid sequence listed as SEQ ID NO: 12;

(1-d) a polynucleotide that encodes a protein consisting of an amino acid sequence that is the amino acid sequence listed as SEQ ID NO: 12 having a deletion, substitution, insertion and/or addition of one or more amino acids, and having the same activity as a protein encoded by the polynucleotide of (1-c); and (1-e) a polynucleotide that encodes a protein having an amino acid sequence with at least 90% identity with respect to the amino acid sequence listed as SEQ ID NO: 12 and having the same activity as a protein encoded by the polynucleotide of (1-c).

[4] The vector according to [3], wherein the *Arabidopsis thaliana* ADH gene-derived untranslated region (5'-UTR) (SEQ ID NO: 15) or the *Arabidopsis thaliana* HSPRO gene-derived untranslated region (5'-UTR) (SEQ ID NO: 13) has been added to the buckwheat-derived CGT gene or its homolog.

[5] The vector according to [3] or [4], which further comprises a flavanone 2-hydroxylase (F2H) gene or its homolog, and a dehydratase (FDH) gene or its homolog.

[6] The vector according to [5], wherein
the F2H gene or its homolog is selected from the group consisting of:

(2-a) a polynucleotide consisting of the nucleotide sequence listed as SEQ ID NO: 5;

(2-b) a polynucleotide that hybridizes with a polynucleotide consisting of the nucleotide sequence complementary to the nucleotide sequence listed as SEQ ID NO: 5 under stringent conditions and has the same activity as the polynucleotide of (2-a);

(2-c) a polynucleotide that encodes a protein consisting of the amino acid sequence listed as SEQ ID NO: 6;

(2-d) a polynucleotide that encodes a protein consisting of an amino acid sequence that is the amino acid sequence listed as SEQ ID NO: 6 having a deletion, substitution, insertion and/or addition of one or more amino acids, and having the same activity as a protein encoded by the polynucleotide of (2-c); and (2-e) a polynucleotide that encodes a protein having an amino acid sequence with at least 90% identity with respect to the amino acid sequence listed as SEQ ID NO: 6 and having the same activity as a protein encoded by the polynucleotide of (2-c), and the FDH gene or its homolog is selected from the group consisting of:

(3-a) a polynucleotide consisting of the nucleotide sequence listed as SEQ ID NO: 9;

(3-b) a polynucleotide that hybridizes with a polynucleotide consisting of the nucleotide sequence complementary to the nucleotide sequence listed as SEQ ID NO: 9 under stringent conditions and has the same activity as the polynucleotide of (3-a);

(3-c) a polynucleotide that encodes a protein consisting of the amino acid sequence listed as SEQ ID NO: 10;

(3-d) a polynucleotide that encodes a protein consisting of an amino acid sequence that is the amino acid sequence listed as SEQ ID NO: 10 having a deletion, substitution, insertion and/or addition of one or more amino acids, and having the same activity as a protein encoded by the polynucleotide of (3-c); and (3-e) a polynucleotide that encodes a protein having an amino acid sequence with at least 90% identity with respect to the amino acid sequence listed as SEQ ID NO: 10 and having the same activity as a protein encoded by the polynucleotide of (3-c).

[7] The vector according to any one of [3] to [6], which further includes a flavonoid F3',5' hydroxylase (F3',5'H) gene or its homolog, and a methyltransferase (MT) gene or its homolog.

[8] The vector according to [7], wherein
the F3',5'H gene or its homolog is selected from the group consisting of:

(4-a) a polynucleotide consisting of the nucleotide sequence listed as SEQ ID NO: 1;

(4-b) a polynucleotide that hybridizes with a polynucleotide consisting of the nucleotide sequence complementary to the nucleotide sequence listed as SEQ ID NO: 1 under stringent conditions and has the same activity as the polynucleotide of (4-a);

(4-c) a polynucleotide that encodes a protein consisting of the amino acid sequence listed as SEQ ID NO: 2;

(4-d) a polynucleotide that encodes a protein consisting of an amino acid sequence that is the amino acid sequence listed as SEQ ID NO: 2 having a deletion, substitution, insertion and/or addition of one or more amino acids, and having the same activity as a protein encoded by the polynucleotide of (4-c); and (4-e) a polynucleotide that encodes a protein having an amino acid sequence with at least 90% identity with respect to the amino acid sequence listed as SEQ ID NO: 2 and having the same activity as a protein encoded by the polynucleotide of (4-c), and the MT gene or its homolog is selected from the group consisting of:

(5-a) a polynucleotide consisting of the nucleotide sequence listed as SEQ ID NO: 3;

(5-b) a polynucleotide that hybridizes with a polynucleotide consisting of the nucleotide sequence complementary to the nucleotide sequence listed as SEQ ID NO: 3 under stringent conditions and has the same activity as the polynucleotide of (5-a);

(5-c) a polynucleotide that encodes a protein consisting of the amino acid sequence listed as SEQ ID NO: 4;

(5-d) a polynucleotide that encodes a protein consisting of an amino acid sequence that is the amino acid sequence listed as SEQ ID NO: 4 having a deletion, substitution, insertion and/or addition of one or more amino acids, and having the same activity as a protein encoded by the polynucleotide of (5-c); and (5-e) a polynucleotide that encodes a protein having an amino acid sequence with at least 90% identity with respect to the amino acid sequence listed as SEQ ID NO: 4 and having the same activity as a protein encoded by the polynucleotide of (5-c).

[9] A transgenic plant comprising a buckwheat-derived CGT gene or its homolog according to [1] or [2] or a vector according to any one of [3] to [8], or its inbred or outbred progeny.

[10] The transgenic plant according to [9], or its inbred or outbred progeny, wherein the plant is selected from among rose, chrysanthemum, carnation or lily.

[11] The transgenic plant according to [10], or its inbred or outbred progeny, wherein the plant is rose.

[12] Propagules, partial plant bodies, tissue or cells of a transgenic plant according to any one of [9] to [11] or its inbred or outbred progeny.

[13] Cut flowers of a transgenic plant according to any one of [9] to [11], or its inbred or outbred progeny, or a processed form created from the cut flowers.

[14] A method for creating transgenic plants with blue flower color, comprising a step of transferring a buckwheat-derived C-glucosyltransferase (CGT) gene or its homolog into a host plant to cause delphinidin-type anthocyanins and flavone mono-C-glycosides to coexist in the plant cells.

[15] The method according to [14], wherein the flavone mono-C-glycoside is apigenin 6-C-glucoside, luteolin 6-C-glucoside, tricetin 6-C-glucoside, apigenin 8-C-glucoside, luteolin 8-C-glucoside or tricetin 8-C-glucoside, or a derivative thereof.

[16] The method according to [14] or [15], wherein the delphinidin-type anthocyanin is selected from the group consisting of malvidins, delphinidins, petunidins and their combinations.

[17] The method according to any one of [14] to [16], which further comprises transferring a buckwheat-derived CGT gene or its homolog according to [1] or [2] or a vector according to any one of [3] to [8] into host plant cells.

[18] The method according to any one of [14] to [17], wherein the plant is rose, chrysanthemum, carnation or lily.

[19] The method according to [18], wherein the plant is rose.

Advantageous Effects of Invention

According to the invention it is possible to uniformly and stably create a plant variety having a blue flower color (RHS Color Chart 5th Edition: Violet-Blue group/Blue group and/or hue angle: 339.7°-270.0°).

Anthocyanins are a group of pigments that are widely extant in plants, and they are known to exhibit red, blue and purple flower colors. They are classified into 3 types, pelargonidin, cyanidin and delphinidin, based on the number of hydroxyl groups on the B-ring of the anthocyanidin, as the aglycone form. The chromophoric group is the aglycone portion, with pelargonidin-type anthocyanins exhibiting orange color, cyanidin-type anthocyanins exhibiting red color and delphinidin-type anthocyanins exhibiting purple to blue color. Throughout the present specification, "delphinidin-type anthocyanins" also include their derivatives having delphinidin, malvidin or petunidin backbones, with malvidin being preferred.

When delphinidin-type anthocyanins are copresent with substances such as flavones, flavonols, organic acid esters and tannins, their molecular interaction often produces blueish colors. This phenomenon is known as "copigmentation", and substances that produce the phenomenon are known as copigments. Copigmentation includes not only a color depth effect that induces blue color production, but also a deep color effect or an effect of increasing color stability. The present inventors have confirmed that copigmentation between delphinidin-type anthocyanins and flavone C-glycosides causes blue color expression in rose petals (PTL 2).

Flavones are organic compounds that are flavan-derived cyclic ketones, and in plants they mainly exist as glycosides. Flavone, in the strict definition, refers to 2,3-didehydroflavan-4-one, which is a compound with chemical formula $C_{15}H_{10}O_2$ and molecular weight 222.24, but in the wider sense flavones are a category of flavonoids, a flavonoid being classified as a "flavone" if it has a flavone structure as the basic backbone and also lacks the hydroxyl group at the 3-position. As used herein, "flavone C-glycoside" means a glycoside of a flavone in the wide sense, i.e. a derivative falling under the definition of flavones, wherein an aglycone is directly bonded to the anomeric carbon of an aldose. Flavone C-glycosides include, but are not limited to, luteolin C-glycoside, tricetin C-glycoside, apigenin C-glycoside and acacetin C-glycoside.

Figure 1:
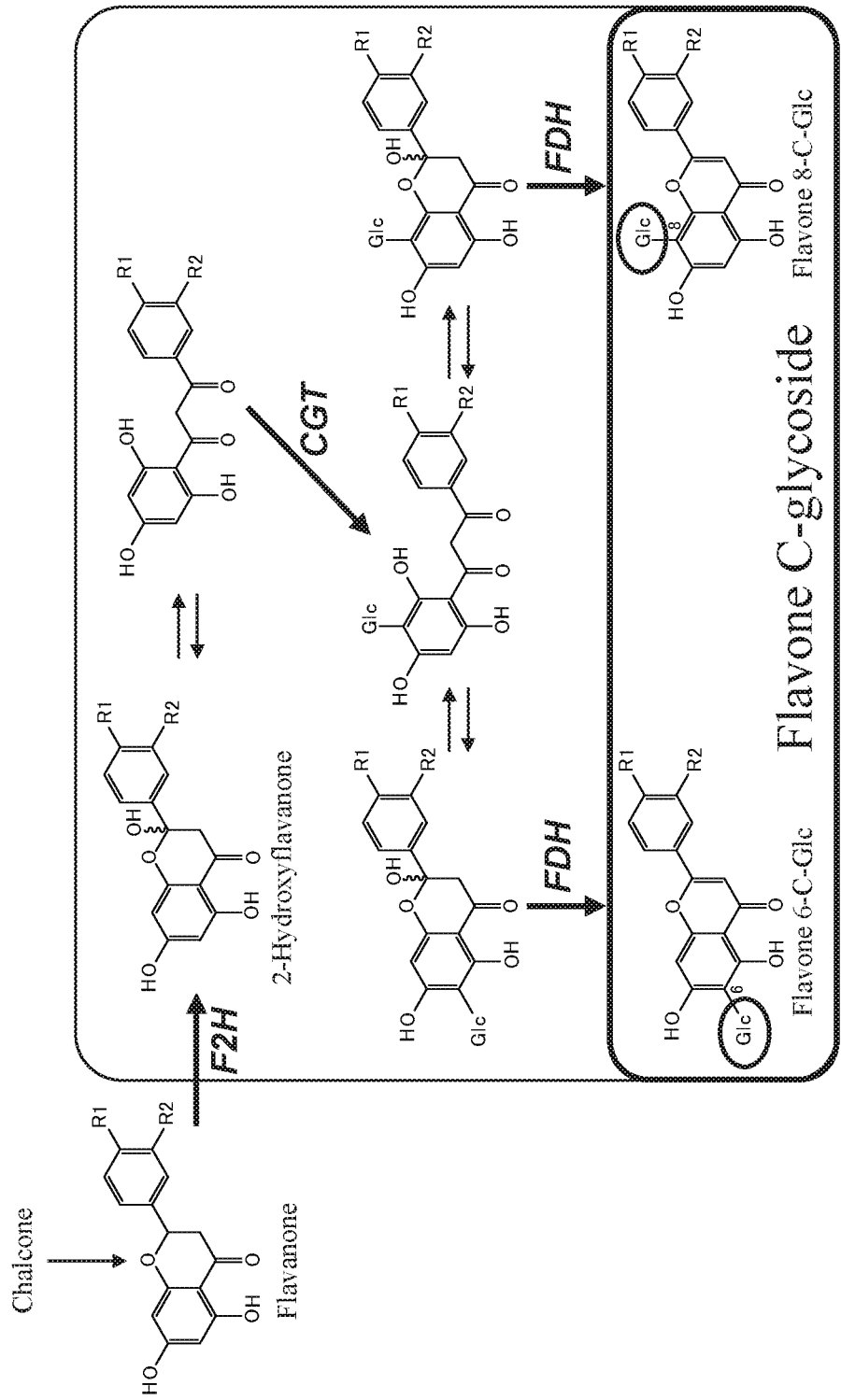
FIG. 1 shows the biosynthetic pathway for a flavone mono-C-glycoside in a plant.
Figure 2:
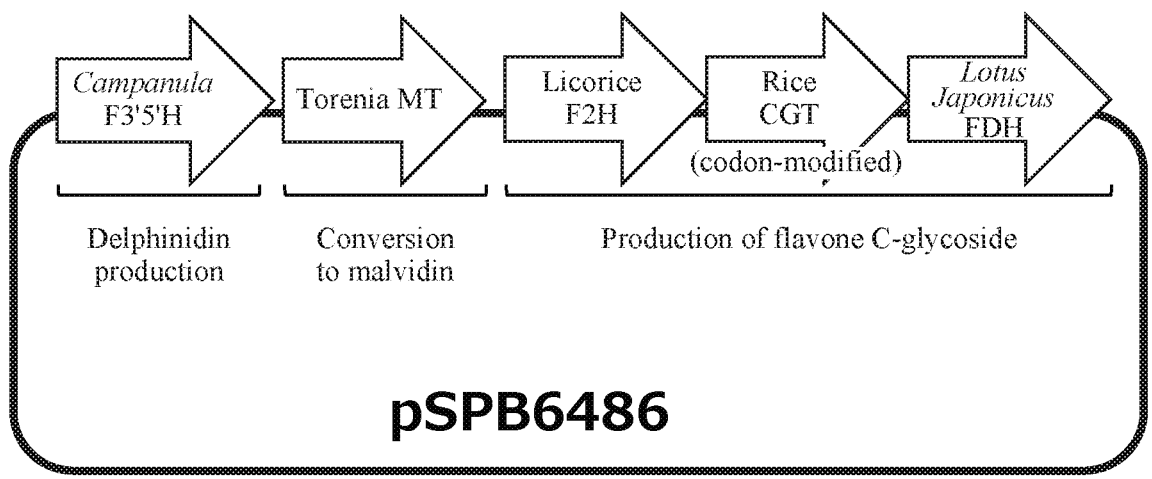
FIG. 2 shows the structure of pSPB6486.
Figure 3:
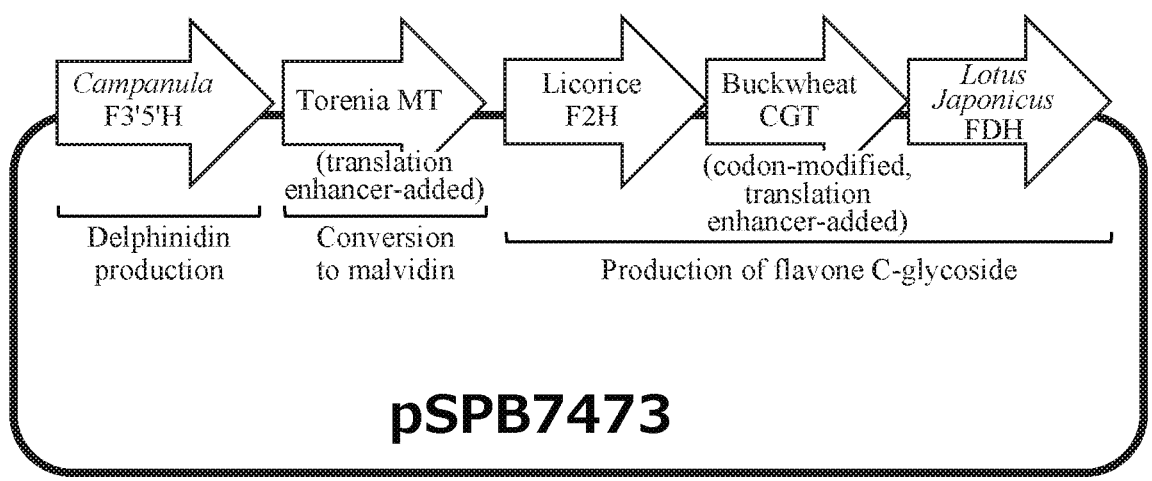
FIG. 3 shows the structure of pSPB7473.
Figure 4:
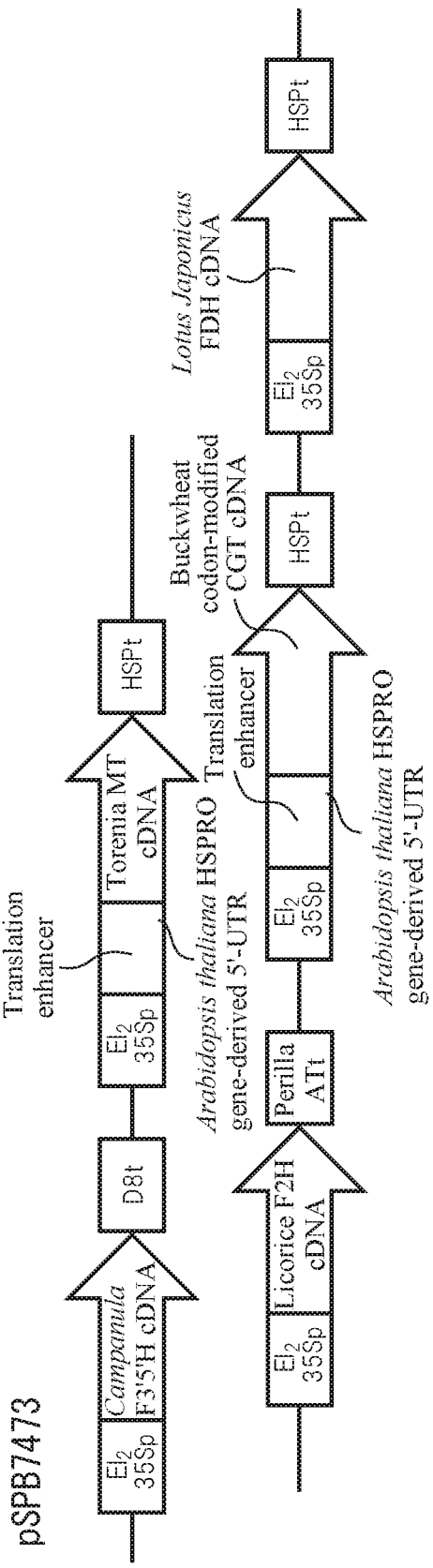
FIG. 4 shows the detailed structured of pSPB7473.
Figure 5:
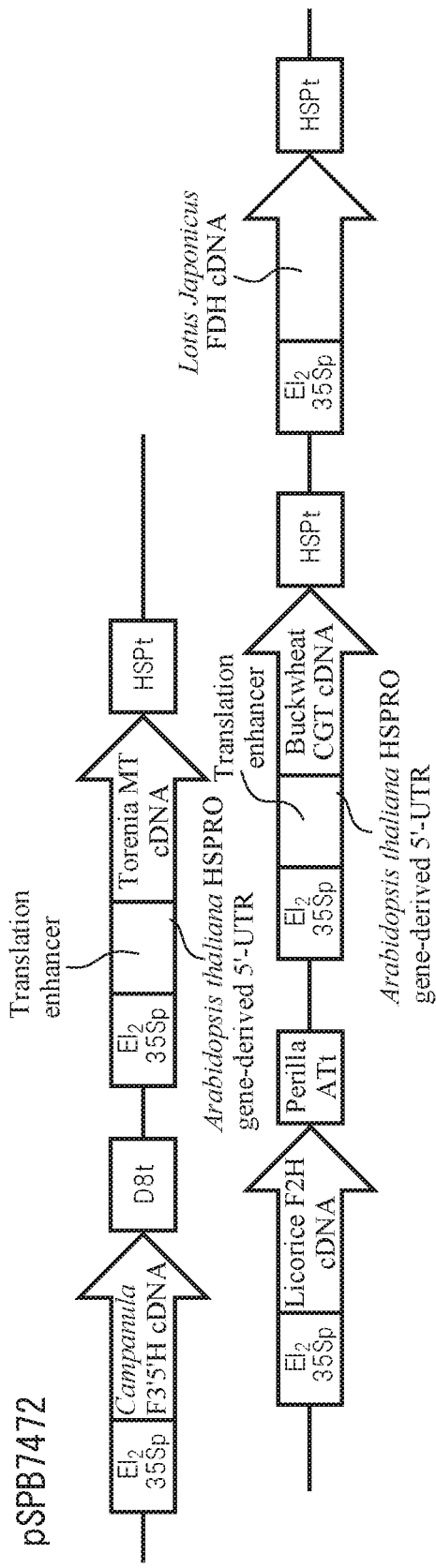
FIG. 5 shows the detailed structured of pSPB7472.
Figure 6:
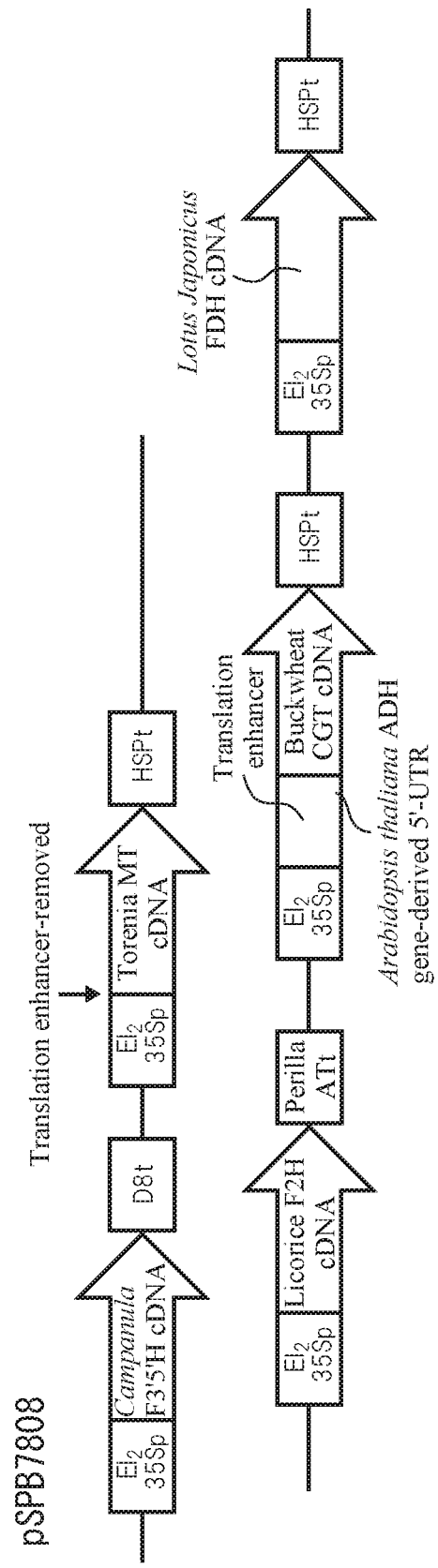
FIG. 6 shows the detailed structured of pSPB7808.
Figure 7:
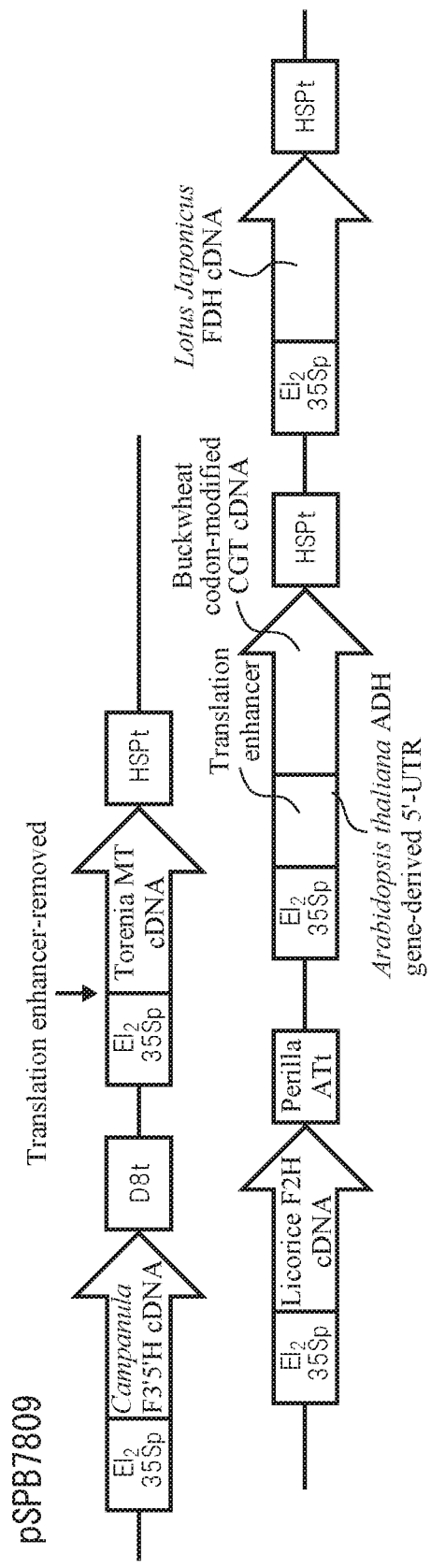
FIG. 7 shows the detailed structured of pSPB7809.

Flavone C-glycosides also include glycosides of apigenin, luteolin, tricetin and acacetin derivatives. One pathway known for the biosynthetic pathway of flavone C-glycosides in plants is the pathway shown in FIG. 1. In this pathway, flavone C-glycoside is produced via F2H, CGT and FDH.

In this synthesis pathway, flavone di-C-glycosides such as vicenin-2 (apigenin 6,8-di-C-glucoside) are also synthesized in addition to flavone mono-C-glycosides, but the present inventors have found, surprisingly, that flavone di-C-glycosides are a cause of redness, and that flavone mono-C-glycosides have a higher copigment effect with delphinidin-type anthocyanins than flavone di-C-glycosides. In order to uniformly and stably create a transgenic plant with blue flower color, it is necessary to reduce to a minimum the accumulation of flavone di-C-glycosides, and to accumulate significant amounts of flavone mono-C-glycosides alone in the petals. Flavone mono-C-glycosides are typically flavone 6-C-glucosides or flavone 8-C-glucosides, but are preferably flavone 6-C-glucosides. Examples of flavone mono-C-glycosides include apigenin 6-C-glucoside (isovitexin), luteolin 6-C-glucoside (isoorientin), tricetin 6-C-glucoside, apigenin 8-C-glucoside (vitexin), luteolin 8-C-glucoside (orientin) and tricetin 8-C-glucoside, or their derivatives.

Accumulation of flavone C-glycosides in plant cells can be achieved by transforming host plants with vectors comprising genes necessary for the aforementioned synthesis pathways (i.e. the F2H gene, CGT gene and FDH gene), or their homologs. If the CGT gene used is a buckwheat-derived CGT gene or its homolog, and particularly a buckwheat-derived CGT gene or its homolog with the *Arabidopsis thaliana* ADH gene-derived untranslated region (5'-

UTR) (SEQ ID NO: 15) or *Arabidopsis thaliana* HSPRO gene-derived untranslated region (5'-UTR) (SEQ ID NO: 13) added as a translation enhancing sequence, it is possible to accumulate significantly more flavone mono-C-glycosides in petals than flavone di-C-glycosides.

The buckwheat-derived CGT gene or its homolog is selected from the group consisting of the following polynucleotides:

(1-a) a polynucleotide consisting of the nucleotide sequence listed as SEQ ID NO: 11;

(1-b) a polynucleotide that hybridizes with a polynucleotide consisting of the nucleotide sequence complementary to the nucleotide sequence listed as SEQ ID NO: 11 under stringent conditions and has the same activity as the polynucleotide of (1-a);

(1-c) a polynucleotide that encodes a protein consisting of the amino acid sequence listed as SEQ ID NO: 12;

(1-d) a polynucleotide that encodes a protein consisting of an amino acid sequence that is the amino acid sequence listed as SEQ ID NO: 12 having a deletion, substitution, insertion and/or addition of one or more amino acids, and having the same activity as a protein encoded by the polynucleotide of (1-c); and (1-e) a polynucleotide that encodes a protein having an amino acid sequence with at least 90% identity with respect to the amino acid sequence listed as SEQ ID NO: 12 and having the same activity as a protein encoded by the polynucleotide of (1-c).

The source of the F2H gene or its homolog is not particularly restricted so long as it has the desired function, but it is preferably a licorice-derived F2H gene or its homolog, and selected from the group consisting of the following polynucleotides:

(2-a) a polynucleotide consisting of the nucleotide sequence listed as SEQ ID NO: 5;

(2-b) a polynucleotide that hybridizes with a polynucleotide consisting of the nucleotide sequence complementary to the nucleotide sequence listed as SEQ ID NO: 5 under stringent conditions and has the same activity as the polynucleotide of (2-a);

(2-c) a polynucleotide that encodes a protein consisting of the amino acid sequence listed as SEQ ID NO: 6;

(2-d) a polynucleotide that encodes a protein consisting of an amino acid sequence that is the amino acid sequence listed as SEQ ID NO: 6 having a deletion, substitution, insertion and/or addition of one or more amino acids, and having the same activity as a protein encoded by the polynucleotide of (2-c); and (2-e) a polynucleotide that encodes a protein having an amino acid sequence with at least 90% identity with respect to the amino acid sequence listed as SEQ ID NO: 6 and having the same activity as a protein encoded by the polynucleotide of (2-c).

The source of the FDH gene or its homolog is not particularly restricted so long as it has the desired function, but it is preferably a *Lotus japonicus*-derived FDH gene or its homolog, and selected from the group consisting of the following polynucleotides:

(3-a) a polynucleotide consisting of the nucleotide sequence listed as SEQ ID NO: 9;

(3-b) a polynucleotide that hybridizes with a polynucleotide consisting of the nucleotide sequence complementary to the nucleotide sequence listed as SEQ ID NO: 9 under stringent conditions and has the same activity as the polynucleotide of (3-a);

(3-c) a polynucleotide that encodes a protein consisting of the amino acid sequence listed as SEQ ID NO: 10;

(3-d) a polynucleotide that encodes a protein consisting of an amino acid sequence that is the amino acid sequence listed as SEQ ID NO: 10 having a deletion, substitution, insertion and/or addition of one or more amino acids, and having the same activity as a protein encoded by the polynucleotide of (3-c); and (3-e) a polynucleotide that encodes a protein having an amino acid sequence with at least 90% identity with respect to the amino acid sequence listed as SEQ ID NO: 10 and having the same activity as a protein encoded by the polynucleotide of (3-c).

Accumulation of delphinidin-type anthocyanins in plant cells can be achieved by incorporating a flavonoid F3',5' hydroxylase (F3',5'H) gene or its homolog and a methyltransferase (MT) gene or its homolog in a host plant (PTL 3). By transforming a host plant with a vector further comprising a F3',5'H gene or its homolog and an MT gene or its homolog in addition to a gene necessary for the synthesis pathway of the aforementioned flavone mono-C-glycosides or their homologs, it is possible to cause a delphinidin-type anthocyanin and a flavone mono-C-glycoside to coexist in the host plant cells.

The source of the F3',5'H gene or its homolog is not particularly restricted so long as it has the desired function, but it is preferably a *Campanula*-derived F3',5'H gene or its homolog, and selected from the group consisting of:

(4-a) a polynucleotide consisting of the nucleotide sequence listed as SEQ ID NO: 1;

(4-b) a polynucleotide that hybridizes with a polynucleotide consisting of the nucleotide sequence complementary to the nucleotide sequence listed as SEQ ID NO: 1 under stringent conditions and has the same activity as the polynucleotide of (4-a);

(4-c) a polynucleotide that encodes a protein consisting of the amino acid sequence listed as SEQ ID NO: 2;

(4-d) a polynucleotide that encodes a protein consisting of an amino acid sequence that is the amino acid sequence listed as SEQ ID NO: 2 having a deletion, substitution, insertion and/or addition of one or more amino acids, and having the same activity as a protein encoded by the polynucleotide of (4-c); and (4-e) a polynucleotide that encodes a protein having an amino acid sequence with at least 90% identity with respect to the amino acid sequence listed as SEQ ID NO: 2 and having the same activity as a protein encoded by the polynucleotide of (4-c).

The source of the MT gene or its homolog is not particularly restricted so long as it has the desired function, but it is preferably a torenia-derived MT gene or its homolog, and selected from the group consisting of:

(5-a) a polynucleotide consisting of the nucleotide sequence listed as SEQ ID NO: 3;

(5-b) a polynucleotide that hybridizes with a polynucleotide consisting of the nucleotide sequence complementary to the nucleotide sequence listed as SEQ ID NO: 3 under stringent conditions and has the same activity as the polynucleotide of (5-a);

(5-c) a polynucleotide that encodes a protein consisting of the amino acid sequence listed as SEQ ID NO: 4;

(5-d) a polynucleotide that encodes a protein consisting of an amino acid sequence that is the amino acid sequence listed as SEQ ID NO: 4 having a deletion, substitution, insertion and/or addition of one or more amino acids, and having the same activity as a protein encoded by the polynucleotide of (5-c); and (5-e) a polynucleotide that encodes a protein having an amino acid sequence with at least 90% identity with respect to the amino acid sequence listed as SEQ ID NO: 4 and having the same activity as a protein encoded by the polynucleotide of (5-c).

The *Arabidopsis thaliana* ADH gene-derived untranslated region (5'-UTR) (SEQ ID NO: 15) or the *Arabidopsis thaliana* HSPRO gene-derived untranslated region (5'-UTR) (SEQ ID NO: 13) may also be added as a translation enhancing sequence to the MT gene or its homolog.

Throughout the present specification, the term "polynucleotide" refers to DNA or RNA.

As used herein, the term "stringent conditions" refers to conditions that allow specific binding between a polynucleotide or oligonucleotide and genomic DNA in a selective and detectable manner. Stringent conditions are defined by an appropriate combination of salt concentration, organic solvent (for example, formamide), temperature and other known conditions. Specifically, stringency is increased by reducing the salt concentration, increasing the organic solvent concentration or raising the hybridization temperature. Stringency is also affected by the rinsing conditions after hybridization. The rinsing conditions are defined by the salt concentration and temperature, and stringency of rinsing is increased by reducing the salt concentration and raising the temperature. Therefore, the term "stringent conditions" means conditions such that specific hybridization takes place only between nucleotide sequences with high identity, such as a degree of "identity" between the nucleotide sequences of about 80% or greater, preferably about 90% or greater, more preferably about 95% or greater, even more preferably 97% or greater and most preferably 98% or greater, on average. The "stringent conditions" may be, for example, a temperature of 60° C. to 68° C., a sodium concentration of 150 to 900 mM and preferably 600 to 900 mM, and a pH of 6 to 8, with specific examples including hybridization under conditions of 5×SSC (750 mM NaCl, 75 mM trisodium citrate), 1% SDS, 5×Denhardt solution, 50% formaldehyde, 42° C., and rinsing under conditions of 0.1×SSC (15 mM NaCl, 1.5 mM trisodium citrate), 0.1% SDS, 55° C.

The hybridization may be carried out by a method that is publicly known in the field or a similar method, such as the method described in Current Protocols in Molecular Biology (edited by Frederick M. Ausubel et al., 1987). When a commercially available library is to be used, the hybridization may be carried out according to the method described in the accompanying directions for use. The gene selected by hybridization may be naturally derived, such as plant-derived or non-plant-derived. The gene selected by the hybridization may be cDNA, genomic DNA or chemically synthesized DNA.

The phrase "amino acid sequence having a deletion, substitution, insertion and/or addition of one or more amino acids", as used herein, means an amino acid sequence having a deletion, substitution, insertion and/or addition of 1 to 20, preferably 1 to 5 and more preferably 1 to 3 arbitrary amino acids. Site-specific mutagenesis is a useful genetic engineering method as it allows introduction of specific mutations into specified sites, and it may be carried out by the method described in Molecular Cloning: A Laboratory Manual, $2^{nd}$ Ed., Cold Spring Harbor Laboratory Press, Cold Spring Harbor, N.Y., 1989. By expressing the mutant DNA using a suitable expression system, it is possible to obtain a protein consisting of an amino acid sequence having a deletion, substitution, insertion and/or addition of one or more amino acids.

A polynucleotide can be obtained by a method that is publicly known to those skilled in the art, such as a method of chemical synthesis using the phosphoramidite method, or a nucleic acid amplification method using a plant nucleic acid specimen as template, and primers designed based on the nucleotide sequence of the target gene.

Throughout the present specification, the term "identity" means, for polypeptide sequences (or amino acid sequences) or polynucleotide sequences (or nucleotide sequences), the quantity (number) of amino acid residues or nucleotides composing them that can be determined to be identical between the two chains, in the sense of mutual agreement between them, meaning the degree of sequence correlation between two polypeptide sequences or two polynucleotide sequences, and this "identity" can be easily calculated. Numerous methods are known for measuring identity between two polynucleotide sequences or polypeptide sequences, and the term "identity" is well known to those skilled in the art (for example, see Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991) and elsewhere).

Also, the numerical values for "identity" used in the present specification, unless otherwise specified, may be the numerical values calculated using an identity search program known to those skilled in the art, but they are preferably numerical values calculated using the ClustalW program of MacVector Application (version 9.5, Oxford Molecular Ltd., Oxford, England). According to the invention, the degree of "identity" between polynucleotide sequences or amino acid sequences is, for example, about 90% or greater, preferably about 95% or greater, more preferably about 97% or greater, and most preferably about 98% or greater.

The polynucleotide (nucleic acid, gene) of the invention "encodes" a protein of interest. Here, "encodes" means that it allows expression of the protein of interest in a state in which it exhibits its activity. Also, the term "encodes" includes both encoding a structural sequence (exon) that is a continuous section of the protein of interest, and encoding via an intervening sequence (intron).

A gene with a natural nucleotide sequence can be obtained by analysis using a DNA sequencer, for example. Also, DNA encoding an enzyme having a modified amino acid sequence can be synthesized using common site-specific mutagenesis or PCR, based on DNA having the natural nucleotide sequence. For example, a DNA fragment to be modified may be obtained by restriction enzyme treatment of natural cDNA or genomic DNA, and used as template for site-specific mutagenesis or PCR using primers with the desired mutation, to obtain a DNA fragment having the desired modification. The DNA fragment having the mutation may then be linked with a DNA fragment encoding another portion of the target enzyme.

Alternatively, in order to obtain DNA encoding an enzyme consisting of a shortened amino acid sequence, DNA encoding an amino acid sequence longer than the target amino acid sequence, such as the full-length amino acid sequence, may be cut with a desired restriction enzyme, and if the obtained DNA fragment does not code for the full target amino acid sequence, then a DNA fragment consisting of the sequence of the missing portion may be synthesized and linked to it.

By expressing the obtained polynucleotide using a gene expression system in *Escherichia coli* or yeast and measuring the enzyme activity, it is possible to confirm that the obtained polynucleotide encodes a protein with the desired activity.

The present invention relates to a (recombinant) vector, and especially an expression vector, including the aforementioned polynucleotide, and to chrysanthemum plants transformed by the vector.

The vector of the invention also comprises an expression control region, such as a promoter, terminator and replication origin, that are dependent on the type of host plant into which it is introduced. Examples of promoters that constitutively express polynucleotides in plant cells include cauliflower mosaic virus 35S promoter, $El_2 35S$ promoter having two 35S promoter enhancer regions linked together, and the rd29A gene promoter, rbcS promoter and mac-1 promoter. For tissue-specific gene expression, a promoter for a gene expressed specifically in that tissue may be used.

The vector may be created by a common method using a restriction enzyme and ligase. Transformation of a host plant using the expression vector may also be carried out by a common method.

At the current level of technology, it is possible to use techniques to introduce a polynucleotide into a plant and constitutively or tissue-specifically express the polynucleotide. Transfer of the DNA into the plant may be carried out by a method known to those skilled in the art, such as the *Agrobacterium* method, binary vector method, electroporation method, PEG method or particle gun method.

Plants to be used as hosts for the invention are not particularly restricted and may be plants belonging to genus Rosaceae *Rosa*, Compositae *Chrysanthemum*, Caryophyllaceae *Dianthus* (such as carnation) or Liliaceae *Lilium*, among which rose cultivar of Rosaceae Rosa (scientific name: *Rosa hybrida*) is especially preferred. The term "rose plant", as used herein, is a rose cultivar of Rosaceae Rosa (scientific name: *Rosa hybrida*), which is its taxonomical classification. Roses are largely classified as Hybrid Tea, *Floribunda* and *Polyantha* roses based on their tree form and flower size, with the major pigment (anthocyanin) in the petals of all lines being of two types, the cyanidin-type and pelargonidin-type. The type of rose plant used as a host for the invention is not particularly restricted, and any of these varieties or lines are suitable. Examples of rose varieties to be used as hosts include Ocean Song, Noblesse, Rita Perfumera, Cool Water, Fame, Topless and Peach Avalanche.

By means of the present invention it is possible to uniformly and stably create transgenic plants, preferably Rosaceae Rosa, Compositae *Chrysanthemum* and Caryophyllaceae *Dianthus* (carnation), and most preferably rose plants, having blue flower colors. When the obtained transgenic plant is a rose plant, it exhibits a flower color in the Blue group or Violet-Blue group according to the RHS Color Chart, and/or with a hue angle of 339.7° to 270.0°, and more preferably 315° or smaller, in the CIEL*a*b* color system.

The invention still further relates to cut flowers of the obtained transgenic plant or its inbred or outbred progeny, or the propagules, partial plant body, tissue or cells, or a processed form created from the cut flowers (especially processed cut flowers). The processed cut flowers referred to here include pressed flowers formed using cut flowers, or preserved flowers, dry flowers or resin sealed products, with no limitation to these.

The present invention will now be explained in greater detail by examples.

EXAMPLES

Example 1: Simulation of Flavone C-Glycoside Copigment Effect with Anthocyanin (Malvin)

An anthocyanin (malvin) and flavone C-glycoside were prepared to simulate the copigment effect of the flavone C-glycoside on malvin. The malvin (malvidin 3,5-diglucoside) and flavone C-glycosides (vitexin (apigenin 8-C-glucoside), isovitexin (apigenin 6-C-glucoside), orientin (luteolin 8-C-glucoside), isoorientin (luteolin 6-C-glucoside) and vicenin-2 (apigenin 6,8-di-C-glucoside)) used in the experiments were purchased from Nacalai Tesque, Inc.

Each flavone C-glycoside (vitexin, isovitexin, orientin, isoorientin or vicenin-2) was added to the acquired malvin at a 5-molar equivalent concentration in a buffering solution at pH 5.0, and the absorption spectra were measured. The malvin concentration was 0.5 mM.

TABLE 1

Absorption maximum (λmax) and hue angle (°) of malvin solution upon flavone C-glycoside addition

| | | Absorption maximum (λmax) | Hue angle |
|---|---|---|---|
| Isovitexin (apigenin 6-C-glucoside) | 5 equiv. | 576 nm | 298° |
| Vitexin (apigenin 8-C-glucoside) | 5 equiv. | 563 nm | 312° |
| Vicenin-2 (apigenin 6,8-di-C-glucoside) | 5 equiv. | 562 nm | 314° |
| Isoorientin (luteolin 6-C-glucoside) | 5 equiv. | 575 nm | 299° |
| Orientin (luteolin 8-C-glucoside) | 5 equiv. | 570 nm | 307° |
| — | — | 531 nm | 334° |

Addition of a flavone C-glycoside increased the absorbance of the malvin solution and shifted the absorption maximum (λmax) toward the long wavelength end compared to malvin alone, regardless of which flavone C-glycoside was added. This effect was confirmed as a greater shift in absorption maximum toward the long wavelength end in the order: isovitexin >isoorientin >orientin >vitexin >vicenin-2. The hue angle was also confirmed to be smaller in the order: isovitexin >isoorientin >orientin >vitexin >vicenin-2. It was thus demonstrated that the copigment effect of flavone mono-C-glycosides is higher than that of flavone di-C-glycosides. In addition, it was shown that the copigment effect of flavone mono-C-glycosides is particularly high with flavone 6-C-glycosides.

Example 2: Transfer of *Campanula*-Derived F3',5'H Gene, Torenia-Derived MT Gene, Licorice-Derived F2H Gene, Rice-Derived Codon Usage-Modified CGT Gene and *Lotus japonicus*-Derived FDH Gene into Rose Variety "Ocean Song"

Plasmid pSPB6486 has pBINPLUS as the basic backbone, and contains the following four expression cassettes.

(1) $El_2 35S$ promoter, *Campanula*-derived F3',5'H full-length cDNA (SEQ ID NO: 1) and D8 terminator (2) $El_2 35S$ promoter, torenia-derived MT full-length cDNA (SEQ ID NO: 3) and NOS terminator (3) 35S promoter, licorice-derived F2H full-length cDNA (SEQ ID NO: 5) and perilla-derived AT terminator (4) 35S promoter, rice-derived codon usage-modified CGT full-length cDNA (SEQ ID NO: 7) and *Arabidopsis thaliana*-derived HSP terminator (5) 35S promoter, *Lotus japonicus*-derived FDH full-length cDNA (SEQ ID NO: 9) and *Arabidopsis thaliana*-derived HSP terminator This plasmid constitutively expresses the *Campanula* F3',5'H gene, torenia MT gene, licorice F2H gene, rice codon usage-modified CGT gene and *Lotus japonicus* FDH gene in plants.

The constructed plasmid pSPB6486 was introduced into the blue rose variety "Ocean Song", and a total of 27 transformants were obtained. Upon pigment analysis, malvidin storage was confirmed in 26 transformants, with a maximum malvidin content of 74.5% (average: 57.0%). The flavone C-glycosides isovitexin (apigenin 6-C-glucoside), vitexin (apigenin 8-C-glucoside), isoorientin (luteolin 6-C-glucoside), orientin (luteolin 8-C-glucoside) and vicenin-2 (apigenin 6,8-di-C-glucoside) were also identified and quantified. Flavone C-glycosides were detected in all of the transformants in which malvidins were detected, with the flavone di-C-glycoside vicenin-2 as the major detected component. The amounts of production were greater than in the order: vicenin-2>isovitexin >vitexin >isoorientin >orientin, with a maximum total amount of 1.563 mg per 1 g of fresh petal weight. The total amount of flavone C-glycosides was more than about 10 times that of malvidins.

The measured values for representative transformants are shown in Table 2 below.

TABLE 2

| Plant No. | Mal (%) | Anthocyanidin (mg/g) | | | | | Flavonol (mg/g) | | | Flavone (mg/g) | | | Flavone C-glycoside (mg/g) | | | | |
|---|---|---|---|---|---|---|---|---|---|---|---|---|---|---|---|---|---|
| | | Del | Cya | Pet | Pel | Mal | M | Q | K | Tri | Lut | Api | Vic2 | VX | IVX | Ori | Iori |
| Host | 0.0 | 0.000 | 0.024 | 0.000 | 0.000 | 0.000 | 0.000 | 2.883 | 0.586 | 0.000 | 0.000 | 0.000 | 0.000 | 0.000 | 0.000 | 0.000 | 0.000 |
| 1 | 70.8 | 0.024 | 0.000 | 0.009 | 0.000 | 0.080 | 1.225 | 0.077 | 0.023 | 0.000 | 0.013 | 0.010 | 0.187 | 0.205 | 0.505 | 0.009 | 0.073 |
| 2 | 66.2 | 0.025 | 0.000 | 0.007 | 0.000 | 0.062 | 2.453 | 0.181 | 0.020 | 0.009 | 0.047 | 0.029 | 0.743 | 0.109 | 0.319 | 0.027 | 0.077 |
| 3 | 54.6 | 0.022 | 0.006 | 0.008 | 0.000 | 0.050 | 1.058 | 1.381 | 0.515 | 0.000 | 0.000 | 0.000 | 0.896 | 0.093 | 0.219 | 0.000 | 0.015 |
| 4 | 52.7 | 0.020 | 0.003 | 0.007 | 0.000 | 0.035 | 0.858 | 0.482 | 0.178 | 0.000 | 0.003 | 0.006 | 0.429 | 0.174 | 0.354 | 0.007 | 0.035 |
| 5 | 64.0 | 0.028 | 0.000 | 0.009 | 0.000 | 0.065 | 2.045 | 0.168 | 0.063 | 0.000 | 0.000 | 0.000 | 0.586 | 0.130 | 0.299 | 0.002 | 0.030 |
| 6 | 67.7 | 0.028 | 0.000 | 0.007 | 0.000 | 0.074 | 1.593 | 0.455 | 0.115 | 0.011 | 0.010 | 0.009 | 0.795 | 0.126 | 0.355 | 0.018 | 0.050 |
| 7 | 72.1 | 0.027 | 0.000 | 0.008 | 0.000 | 0.089 | 2.753 | 0.526 | 0.183 | 0.006 | 0.004 | 0.004 | 0.905 | 0.093 | 0.262 | 0.000 | 0.028 |
| 8 | 54.7 | 0.019 | 0.007 | 0.005 | 0.000 | 0.049 | 1.010 | 2.128 | 0.418 | 0.018 | 0.002 | 0.005 | 0.945 | 0.226 | 0.325 | 0.000 | 0.021 |
| 9 | 39.1 | 0.018 | 0.009 | 0.004 | 0.000 | 0.025 | 0.679 | 1.438 | 0.322 | 0.005 | 0.002 | 0.002 | 0.672 | 0.246 | 0.283 | 0.007 | 0.020 |
| 10 | 39.8 | 0.013 | 0.009 | 0.005 | 0.000 | 0.021 | 0.447 | 1.129 | 0.586 | 0.000 | 0.000 | 0.002 | 0.432 | 0.080 | 0.179 | 0.000 | 0.010 |
| 11 | 45.9 | 0.011 | 0.011 | 0.006 | 0.000 | 0.034 | 0.914 | 3.471 | 1.481 | 0.000 | 0.000 | 0.000 | 0.839 | 0.050 | 0.118 | 0.000 | 0.003 |
| 12 | 45.4 | 0.022 | 0.005 | 0.007 | 0.000 | 0.032 | 0.803 | 0.992 | 0.418 | 0.000 | 0.004 | 0.005 | 0.511 | 0.142 | 0.354 | 0.000 | 0.024 |
| 13 | 62.8 | 0.032 | 0.000 | 0.008 | 0.000 | 0.067 | 1.830 | 0.210 | 0.059 | 0.018 | 0.023 | 0.015 | 0.910 | 0.000 | 0.249 | 0.000 | 0.049 |
| 14 | 65.6 | 0.024 | 0.000 | 0.007 | 0.000 | 0.060 | 1.942 | 0.258 | 0.078 | 0.011 | 0.019 | 0.015 | 1.047 | 0.056 | 0.305 | 0.016 | 0.054 |
| 15 | 52.9 | 0.042 | 0.002 | 0.009 | 0.000 | 0.062 | 0.993 | 0.377 | 0.100 | 0.000 | 0.004 | 0.005 | 0.396 | 0.197 | 0.450 | 0.000 | 0.050 |
| 16 | 63.9 | 0.031 | 0.000 | 0.007 | 0.000 | 0.067 | 2.742 | 0.221 | 0.056 | 0.009 | 0.030 | 0.018 | 0.591 | 0.063 | 0.285 | 0.022 | 0.058 |
| 17 | 63.5 | 0.016 | 0.000 | 0.005 | 0.000 | 0.037 | 1.767 | 0.102 | 0.013 | 0.009 | 0.051 | 0.029 | 0.621 | 0.147 | 0.242 | 0.022 | 0.061 |
| 18 | 74.5 | 0.029 | 0.000 | 0.009 | 0.000 | 0.109 | 2.078 | 0.187 | 0.029 | 0.017 | 0.030 | 0.015 | 0.604 | 0.051 | 0.276 | 0.021 | 0.061 |
| 19 | 55.4 | 0.019 | 0.009 | 0.006 | 0.000 | 0.059 | 0.937 | 1.893 | 0.502 | 0.008 | 0.001 | 0.000 | 1.002 | 0.078 | 0.218 | 0.000 | 0.007 |
| 20 | 38.5 | 0.006 | 0.010 | 0.002 | 0.000 | 0.019 | 0.480 | 2.621 | 0.468 | 0.007 | 0.001 | 0.003 | 0.890 | 0.147 | 0.247 | 0.000 | 0.012 |
| 21 | 47.7 | 0.025 | 0.000 | 0.009 | 0.000 | 0.031 | 2.684 | 0.376 | 0.102 | 0.008 | 0.019 | 0.018 | 0.700 | 0.147 | 0.303 | 0.017 | 0.048 |
| 22 | 39.5 | 0.011 | 0.013 | 0.003 | 0.000 | 0.026 | 0.497 | 2.333 | 0.524 | 0.000 | 0.004 | 0.008 | 0.720 | 0.224 | 0.346 | 0.009 | 0.030 |
| 23 | 65.3 | 0.019 | 0.001 | 0.007 | 0.000 | 0.055 | 1.615 | 1.007 | 0.223 | 0.005 | 0.001 | 0.000 | 0.828 | 0.101 | 0.207 | 0.000 | 0.013 |
| 24 | 70.0 | 0.028 | 0.000 | 0.008 | 0.000 | 0.087 | 2.776 | 0.531 | 0.166 | 0.000 | 0.001 | 0.000 | 0.913 | 0.055 | 0.178 | 0.000 | 0.012 |
| 25 | 66.2 | 0.014 | 0.003 | 0.007 | 0.000 | 0.058 | 1.428 | 1.898 | 0.525 | 0.000 | 0.008 | 0.014 | 0.907 | 0.255 | 0.368 | 0.000 | 0.034 |
| 26 | 42.7 | 0.036 | 0.017 | 0.011 | 0.000 | 0.063 | 0.991 | 2.495 | 0.457 | 0.000 | 0.000 | 0.000 | 0.529 | 0.030 | 0.094 | 0.000 | 0.000 |

Host: Ocean Song
Del: delphinidin,
Cya: cyanidin,
Pet: petunidin,
Pel: pelargonidin,
Mal: malvidin
M: myricetin,
Q: quercetin,
K: kaempferol
Tri: tricetin,
Lut: luteolin,
Api: apigenin,
Vic2: vicenin-2,
VX: vitexin,
IVX: isovitexin,
Ori: orientin,
Iori: isoorientin
Mal(%): Proportion of malvidin in total anthocyanidins Example 3: Transfer of *Campanula*-Derived F3',5'H Gene, Torenia-Derived MT Gene, Licorice-Derived F2H Gene, Buckwheat-Derived Codon Usage-Modified CGT Gene and *Lotus japonicus*-Derived FDH Gene into Rose Variety "Ocean Song"

Plasmid pSPB7473 has pBINPLUS as the basic backbone, and contains the following four expression cassettes.

(1) El₂35S promoter, *Campanula*-derived F3',5'H full-length cDNA (SEQ ID NO: 1) and D8 terminator (2) El₂35S promoter, torenia-derived MT full-length cDNA (SEQ ID NO: 3) (*Arabidopsis thaliana* HSPRO gene-derived 5'-UTR (SEQ ID NO: 13) added to the 5'-position end) and *Arabidopsis thaliana*-derived HSP terminator (3) El₂35S promoter, licorice-derived F2H full-length cDNA (SEQ ID NO: 5) and *perilla*-derived AT terminator (4) El₂35S promoter, buckwheat-derived codon usage-modified CGT full-length cDNA (SEQ ID NO: 11) (*Arabidopsis thaliana* HSPRO gene-derived 5'-UTR (SEQ ID NO: 13) added to the 5'-position end) and *Arabidopsis thaliana*-derived HSP terminator (5) El₂35S promoter, *Lotus japonicus*-derived FDH full-length cDNA (SEQ ID NO: 9) and *Arabidopsis thaliana*-derived HSP terminator This plasmid constitutively expresses the *Campanula* F3',5'H gene, torenia MT gene, licorice F2H gene, buckwheat codon usage-modified CGT gene and *Lotus japonicus* FDH gene in plants.

The constructed plasmid pSPB7473 was introduced into the blue rose variety "Ocean Song", and a total of 35 transformants were obtained. Upon pigment analysis, malvidin storage was confirmed in 21 transformants, with a maximum malvidin content of 20.8% (average: 9.1%). The flavone C-glycosides isovitexin (apigenin 6-C-glucoside), vitexin (apigenin 8-C-glucoside), isoorientin (luteolin 6-C-glucoside), orientin (luteolin 8-C-glucoside) and vicenin-2 (apigenin 6,8-di-C-glucoside) were also identified and quantified. Flavone C-glycosides were detected in all of the transformants in which malvidins were detected, with the flavone 6-C-glycoside isovitexin as the major detected component. The amounts of production were greater in the order isovitexin >vitexin >vicenin-2>isoorientin >orientin, and the maximum total amount was 7.418 mg per 1 g of fresh petal weight, indicating a very high content. In addition, in comparison to the OS/6486 line described in Example 2, the total amount of flavone C-glycosides was a high content of 3 mg or greater per 1 g of fresh petal weight in most of the transformants, which was at least about 100 times compared to delphinidins.

The measured values for representative transformants are shown in Table 3 below.

TABLE 3

| Plant No. | Anthocyanidin (mg/g fresh weight) | | | | | Flavonol (mg/g fresh weight) | | | | Flavone (mg/g fresh weight) | | | | Flavone C-glycoside (mg/g fresh weight) | | | | Mal (%) | Total flavone C-glycosides (mg/g fresh weight) |
|---|---|---|---|---|---|---|---|---|---|---|---|---|---|---|---|---|---|---|---|
| | Del | Cya | Pet | Pel | Mal | M | Q | K | Tri | Lut | Api | Vic2 | VX | IVX | Ori | Iori | | |
| Host | 0.000 | 0.024 | 0.000 | 0.000 | 0.000 | 0.000 | 2.883 | 0.586 | 0.000 | 0.000 | 0.000 | 0.000 | 0.000 | 0.000 | 0.000 | 0.000 | — | — |
| 1 | 0.053 | 0.001 | 0.005 | 0.000 | 0.003 | 1.261 | 0.220 | 0.044 | 0.029 | 0.000 | 0.000 | 0.922 | 1.500 | 1.927 | 0.083 | 0.169 | 5.4 | 4.601 |
| 2 | 0.065 | 0.000 | 0.007 | 0.000 | 0.003 | 2.520 | 0.130 | 0.051 | 0.042 | 0.000 | 0.000 | 1.773 | 2.140 | 2.893 | 0.141 | 0.288 | 4.2 | 7.235 |
| 3 | 0.086 | 0.004 | 0.009 | 0.000 | 0.005 | 1.459 | 0.419 | 0.093 | 0.000 | 0.000 | 0.000 | 1.160 | 1.777 | 2.203 | 0.082 | 0.165 | 4.8 | 5.387 |
| 4 | 0.054 | 0.000 | 0.008 | 0.000 | 0.009 | 2.885 | 0.168 | 0.032 | 0.000 | 0.000 | 0.000 | 0.041 | 0.000 | 0.000 | 0.000 | 0.000 | 13.0 | 0.041 |
| 5 | 0.063 | 0.000 | 0.009 | 0.000 | 0.007 | 2.903 | 0.186 | 0.055 | 0.041 | 0.000 | 0.000 | 1.787 | 2.255 | 2.962 | 0.138 | 0.276 | 8.7 | 7.418 |
| 6 | 0.009 | 0.004 | 0.002 | 0.000 | 0.002 | 1.096 | 2.107 | 0.345 | 0.026 | 0.000 | 0.026 | 1.093 | 1.774 | 2.711 | 0.095 | 0.177 | 9.6 | 5.849 |
| 7 | 0.012 | 0.008 | 0.002 | 0.000 | 0.001 | 0.683 | 1.642 | 0.173 | 0.025 | 0.000 | 0.015 | 0.800 | 1.192 | 1.648 | 0.063 | 0.138 | 6.2 | 3.840 |
| 8 | 0.011 | 0.001 | 0.003 | 0.000 | 0.002 | 1.737 | 0.984 | 0.164 | 0.029 | 0.000 | 0.010 | 0.990 | 1.582 | 2.389 | 0.100 | 0.195 | 12.5 | 5.256 |
| 9 | 0.026 | 0.016 | 0.002 | 0.000 | 0.001 | 0.723 | 1.928 | 0.181 | 0.000 | 0.000 | 0.012 | 0.796 | 1.080 | 1.320 | 0.000 | 0.114 | 3.0 | 3.310 |
| 10 | 0.022 | 0.008 | 0.002 | 0.000 | 0.002 | 1.017 | 1.325 | 0.309 | 0.000 | 0.000 | 0.000 | 1.394 | 1.442 | 2.123 | 0.070 | 0.136 | 5.5 | 5.165 |
| 11 | 0.040 | 0.000 | 0.004 | 0.000 | 0.002 | 1.706 | 0.177 | 0.060 | 0.019 | 0.000 | 0.000 | 0.851 | 1.086 | 1.541 | 0.068 | 0.129 | 4.1 | 3.674 |
| 12 | 0.035 | 0.000 | 0.003 | 0.000 | 0.002 | 1.898 | 0.219 | 0.069 | 0.023 | 0.000 | 0.000 | 1.000 | 1.328 | 1.892 | 0.082 | 0.165 | 4.6 | 4.466 |
| 13 | 0.031 | 0.000 | 0.004 | 0.000 | 0.003 | 0.888 | 0.041 | 0.012 | 0.027 | 0.004 | 0.000 | 1.120 | 1.482 | 1.939 | 0.091 | 0.194 | 7.8 | 4.826 |
| 14 | 0.040 | 0.000 | 0.005 | 0.000 | 0.005 | 0.980 | 0.048 | 0.017 | 0.024 | 0.000 | 0.000 | 1.153 | 1.387 | 1.757 | 0.087 | 0.183 | 9.1 | 4.568 |
| 15 | 0.027 | 0.000 | 0.007 | 0.000 | 0.009 | 1.273 | 0.108 | 0.030 | 0.000 | 0.000 | 0.000 | 0.533 | 1.386 | 1.402 | 0.059 | 0.122 | 20.8 | 3.501 |
| 16 | 0.020 | 0.000 | 0.005 | 0.000 | 0.006 | 1.567 | 0.129 | 0.045 | 0.025 | 0.000 | 0.008 | 0.610 | 1.523 | 1.819 | 0.084 | 0.165 | 18.9 | 4.200 |
| 17 | 0.018 | 0.051 | 0.003 | 0.000 | 0.004 | 0.188 | 1.761 | 0.118 | 0.000 | 0.000 | 0.000 | 0.705 | 0.409 | 0.632 | 0.016 | 0.043 | 5.1 | 1.806 |
| 18 | 0.014 | 0.035 | 0.002 | 0.000 | 0.004 | 0.242 | 2.042 | 0.265 | 0.010 | 0.000 | 0.000 | 1.008 | 0.682 | 1.022 | 0.034 | 0.066 | 7.7 | 2.813 |
| 19 | 0.021 | 0.028 | 0.005 | 0.000 | 0.014 | 0.339 | 1.434 | 0.167 | 0.012 | 0.000 | 0.000 | 0.935 | 0.919 | 1.241 | 0.037 | 0.081 | 19.7 | 3.214 |
| 20 | 0.014 | 0.033 | 0.002 | 0.000 | 0.006 | 0.236 | 1.697 | 0.204 | 0.000 | 0.000 | 0.000 | 1.155 | 0.839 | 1.265 | 0.036 | 0.086 | 10.0 | 3.381 |
| 21 | 0.045 | 0.001 | 0.006 | 0.000 | 0.006 | 1.641 | 0.302 | 0.087 | 0.018 | 0.000 | 0.000 | 0.987 | 1.066 | 1.296 | 0.051 | 0.099 | 10.9 | 3.499 |
| Average | | | | | | | | | | | | | | | | | 9.1 | 4.193 |
| S.D. | | | | | | | | | | | | | | | | | 5.3 | 1.663 |

Host: Ocean Song
Del: delphinidin,
Cya: cyanidin,
Pet: petunidin,
Pel: pelargonidin,
Mal: malvidin
M: myricetin,
Q: quercetin,
K: kaempferol
Tri: tricetin,
Lut: luteolin,
Api: apigenin,
Vic2: vicenin-2,
VX: vitexin,
IVX: isovitexin,
Ori: orientin,
Iori: isoorientin
Mal(%): Proportion of malvidin in total anthocyanidins Example 4: Transfer of *Campanula*-Derived F3',5'H Gene, Torenia-Derived MT Gene, Licorice-Derived F2H Gene, Buckwheat-Derived CGT Gene and *Lotus japonicus*-Derived FDH Gene into Rose Variety "Ocean Song"

Plasmid pSPB7472 has pBINPLUS as the basic backbone, and contains the following four expression cassettes.

(1) El$_2$35S promoter, *Campanula*-derived F3',5'H full-length cDNA (SEQ ID NO: 1) and D8 terminator (2) El$_2$35S promoter, torenia-derived MT full-length cDNA (SEQ ID NO: 3) (*Arabidopsis thaliana* HSPRO gene-derived 5'-UTR (SEQ ID NO: 13) added to the 5'-position end) and *Arabidopsis thaliana*-derived HSP terminator (3) El$_2$35S promoter, licorice-derived F2H full-length cDNA (SEQ ID NO: 5) and *perilla*-derived AT terminator (4) El$_2$35S promoter, buckwheat-derived CGT full-length cDNA (SEQ ID NO: 14) (*Arabidopsis thaliana* HSPRO gene-derived 5'-UTR (SEQ ID NO: 13)) added to the 5'-position end) and *Arabidopsis thaliana*-derived HSP terminator (5) El$_2$35S promoter, *Lotus japonicus*-derived FDH full-length cDNA (SEQ ID NO: 9) and *Arabidopsis thaliana*-derived HSP terminator This plasmid constitutively expresses the *Campanula* F3',5'H gene, torenia MT gene, licorice F2H gene, buckwheat CGT gene and *Lotus japonicus* FDH gene in plants.

The constructed plasmid pSPB7472 was introduced into the blue rose variety "Ocean Song", and a total of 33 transformants were obtained. The flavone C-glycosides isovitexin (apigenin 6-C-glucoside), vitexin (apigenin 8-C-glucoside), isoorientin (luteolin 6-C-glucoside), orientin (luteolin 8-C-glucoside) and vicenin-2 (apigenin 6,8-di-C-glucoside), and the anthocyanidins delphinidin, cyanidin, petunidin, pelargonidin and malvidin, were then identified and quantified. As a result, accumulation of flavone C-glycosides and malvidin was confirmed in 11 transformants. The average content of flavone C-glycosides was 3.75 mg per 1 g of fresh petal weight, with the flavone 6-C-glycoside isovitexin detected as the main component. The malvidin content was a maximum of 15.6% (average: 8.8%).

Thus, the average content of flavone C-glycosides per 1 g of fresh petal weight was higher in the OS/7473 line described in Example 3, at 4.19 mg. In other words, it is possible to produce flavone C-glycosides more efficiently with the codon-modified CGT gene than with the original buckwheat-derived CGT gene.

The measured values for representative transformants are shown in Table 4 below.

TABLE 4

| Plant | Anthocyanidin (mg/g fresh weight) | | | | Flavonol (mg/g fresh weight) | | | | Flavone (mg/g fresh weight) | | | | Flavone C-glycoside (mg/g fresh weight) | | | | Mal | Total flavone C-gly cosides (mg/g fresh |
|---|---|---|---|---|---|---|---|---|---|---|---|---|---|---|---|---|---|---|
| No. | Del | Cya | Pet | Pel | Mal | M | Q | K | Tri | Lut | Api | Vic2 | VX | IVX | Ori | Iori | (%) | weight) |
| Host | 0.000 | 0.024 | 0.000 | 0.000 | 0.000 | 0.000 | 2.883 | 0.586 | 0.000 | 0.000 | 0.000 | 0.000 | 0.000 | 0.000 | 0.000 | 0.000 | — | — |
| 1 | 0.120 | 0.000 | 0.027 | 0.000 | 0.027 | 2.784 | 0.211 | 0.029 | 0.000 | 0.000 | 0.000 | 0.061 | 0.000 | 0.000 | 0.000 | 0.000 | 15.6 | 0.061 |
| 2 | 0.041 | 0.000 | 0.007 | 0.000 | 0.003 | 2.485 | 0.369 | 0.094 | 0.036 | 0.000 | 0.000 | 1.010 | 1.873 | 2.654 | 0.107 | 0.221 | 6.8 | 5.864 |
| 3 | 0.100 | 0.002 | 0.008 | 0.000 | 0.002 | 1.632 | 0.316 | 0.055 | 0.000 | 0.000 | 0.000 | 1.244 | 2.093 | 2.482 | 0.103 | 0.204 | 1.9 | 6.127 |
| 4 | 0.025 | 0.000 | 0.002 | 0.000 | 0.001 | 1.916 | 0.221 | 0.060 | 0.026 | 0.000 | 0.000 | 0.872 | 1.545 | 2.228 | 0.104 | 0.200 | 4.1 | 4.950 |
| 5 | 0.031 | 0.000 | 0.005 | 0.000 | 0.003 | 2.125 | 0.298 | 0.076 | 0.021 | 0.000 | 0.000 | 0.847 | 1.400 | 1.937 | 0.075 | 0.156 | 6.7 | 4.415 |
| 6 | 0.039 | 0.000 | 0.008 | 0.000 | 0.005 | 1.926 | 0.251 | 0.072 | 0.000 | 0.000 | 0.000 | 0.717 | 1.292 | 1.731 | 0.070 | 0.143 | 8.9 | 3.953 |
| 7 | 0.043 | 0.000 | 0.004 | 0.000 | 0.003 | 1.117 | 0.126 | 0.031 | 0.024 | 0.000 | 0.000 | 1.304 | 1.365 | 1.781 | 0.082 | 0.177 | 5.3 | 4.710 |
| 8 | 0.053 | 0.002 | 0.010 | 0.000 | 0.010 | 0.968 | 0.143 | 0.023 | 0.000 | 0.000 | 0.000 | 0.982 | 1.064 | 1.495 | 0.062 | 0.129 | 13.2 | 3.732 |
| 9 | 0.016 | 0.000 | 0.005 | 0.000 | 0.004 | 1.759 | 0.175 | 0.083 | 0.000 | 0.000 | 0.000 | 0.661 | 0.941 | 2.106 | 0.100 | 0.174 | 14.9 | 3.982 |
| 10 | 0.014 | 0.000 | 0.004 | 0.000 | 0.003 | 1.618 | 0.148 | 0.088 | 0.000 | 0.000 | 0.000 | 0.651 | 0.820 | 1.741 | 0.000 | 0.153 | 13.4 | 3.366 |
| 11 | 0.011 | 0.000 | 0.002 | 0.000 | 0.001 | 0.292 | 0.000 | 0.000 | 0.332 | 0.433 | 0.082 | 0.095 | 0.000 | 0.000 | 0.000 | 0.000 | 6.3 | 0.095 |
| Average | | | | | | | | | | | | | | | | | 8.8 | 3.750 |
| S.D. | | | | | | | | | | | | | | | | | 4.7 | 2.003 |

Host: Ocean Song
Del: delphinidin,
Cya: cyanidin,
Pet: petunidin,
Pel: pelargonidin,
Mal: malvidin
M: myricetin,
Q: quercetin,
K: kaempferol
Tri: tricetin,
Lut: luteolin,
Api: apigenin,
Vic2: vicenin-2,
VX: vitexin,
IVX: isovitexin,
Ori: orientin,
Iori: isoorientin
Mal(%): Proportion of malvidin in total anthocyanidins Example 5: Transfer of *Campanula*-Derived F3',5'H Gene, Torenia-Derived MT Gene, Licorice-Derived F2H Gene, Buckwheat-Derived CGT Gene and *Lotus japonicus*-Derived FDH Gene into Rose Variety "Ocean Song"

Plasmid pSPB7808 has pBINPLUS as the basic backbone, and contains the following four expression cassettes.

(1) El$_2$35S promoter, *Campanula*-derived F3',5'H full-length cDNA (SEQ ID NO: 1) and D8 terminator (2) El₂35S promoter, torenia-derived MT full-length cDNA (SEQ ID NO: 3) and *Arabidopsis thaliana*-derived HSP terminator (3) El₂35S promoter, licorice-derived F2H full-length cDNA (SEQ ID NO: 5) and *perilla*-derived AT terminator (4) El₂35S promoter, buckwheat-derived CGT full-length cDNA (SEQ ID NO: 14) (*Arabidopsis thaliana* alcohol dehydrogenase (ADH) gene-derived 5'-UTR (SEQ ID NO: 15) added to the 5'-position end) and *Arabidopsis thaliana*-derived HSP terminator (5) El₂35S promoter, *Lotus japonicus*-derived FDH full-length cDNA (SEQ ID NO: 9) and *Arabidopsis thaliana*-derived HSP terminator This plasmid constitutively expresses the *Campanula* F3',5'H gene, torenia MT gene, licorice F2H gene, buckwheat CGT gene and *Lotus japonicus* FDH gene in plants.

The constructed plasmid pSPB7808 was introduced into the blue rose variety "Ocean Song", and a total of 65 transformants were obtained. The flavone C-glycosides isovitexin (apigenin 6-C-glucoside), vitexin (apigenin 8-C-glucoside), isoorientin (luteolin 6-C-glucoside), orientin (luteolin 8-C-glucoside) and vicenin-2 (apigenin 6,8-di-C-glucoside), and the anthocyanidins delphinidin, cyanidin, petunidin, pelargonidin and malvidin, were then identified and quantified. As a result, accumulation of flavone C-glycosides and malvidin was confirmed in 32 transformants. The mean content of flavone C-glycosides was 3.00 mg per 1 g of fresh petal weight, with the flavone 6-C-glycoside isovitexin detected as the main component. The malvidin content was a maximum of 69.2% (average: 43.9%).

The measured values for representative transformants are shown in Table 5 below.

TABLE 5

| Plant No. | Anthocyanidin (mg/g fresh weight) | | | | Flavonol (mg/g fresh weight) | | | | Flavone (mg/g fresh weight) | | | | Flavone C-glycoside (mg/g fresh weight) | | | | Mal (%) | Total flavone C-glycosides (mg/g fresh weight) |
|---|---|---|---|---|---|---|---|---|---|---|---|---|---|---|---|---|---|---|
| | Del | Cya | Pet | Pel | Mal | M | Q | K | Tri | Lut | Api | Vic2 | VX | IVX | Ori | Iori | | |
| Host | 0.000 | 0.024 | 0.000 | 0.000 | 0.000 | 0.000 | 2.883 | 0.586 | 0.000 | 0.000 | 0.000 | 0.000 | 0.000 | 0.000 | 0.000 | 0.000 | — | — |
| 1 | 0.052 | 0.000 | 0.004 | 0.000 | 0.002 | 0.755 | 0.000 | 0.000 | 0.074 | 0.174 | 0.086 | 0.329 | 1.123 | 2.417 | 0.145 | 0.285 | 3.0 | 4.299 |
| 2 | 0.026 | 0.002 | 0.020 | 0.000 | 0.068 | 1.448 | 0.321 | 0.206 | 0.000 | 0.000 | 0.000 | 0.560 | 0.587 | 1.380 | 0.000 | 0.056 | 57.1 | 2.583 |
| 3 | 0.021 | 0.000 | 0.010 | 0.000 | 0.026 | 1.569 | 0.271 | 0.252 | 0.000 | 0.000 | 0.000 | 0.898 | 0.878 | 1.945 | 0.051 | 0.108 | 46.7 | 3.880 |
| 4 | 0.022 | 0.000 | 0.009 | 0.000 | 0.023 | 1.549 | 0.340 | 0.265 | 0.000 | 0.000 | 0.000 | 0.867 | 0.874 | 1.792 | 0.044 | 0.090 | 42.5 | 3.667 |
| 5 | 0.006 | 0.000 | 0.004 | 0.000 | 0.005 | 0.775 | 0.000 | 0.000 | 0.027 | 0.146 | 0.120 | 0.238 | 0.431 | 1.005 | 0.063 | 0.115 | 34.4 | 1.851 |
| 6 | 0.006 | 0.000 | 0.003 | 0.000 | 0.002 | 0.747 | 0.000 | 0.000 | 0.025 | 0.110 | 0.083 | 0.237 | 0.389 | 0.907 | 0.065 | 0.116 | 18.8 | 1.715 |
| 7 | 0.007 | 0.000 | 0.003 | 0.000 | 0.007 | 1.014 | 0.064 | 0.028 | 0.029 | 0.148 | 0.100 | 0.410 | 0.596 | 1.338 | 0.099 | 0.176 | 41.0 | 2.619 |
| 8 | 0.007 | 0.000 | 0.003 | 0.000 | 0.006 | 1.134 | 0.080 | 0.025 | 0.034 | 0.183 | 0.127 | 0.354 | 0.638 | 1.423 | 0.101 | 0.179 | 36.9 | 2.696 |
| 9 | 0.009 | 0.000 | 0.004 | 0.000 | 0.011 | 1.713 | 0.303 | 0.127 | 0.000 | 0.000 | 0.000 | 0.617 | 0.682 | 1.498 | 0.052 | 0.101 | 46.6 | 2.949 |
| 10 | 0.006 | 0.000 | 0.005 | 0.000 | 0.016 | 1.359 | 0.292 | 0.128 | 0.000 | 0.000 | 0.000 | 0.545 | 0.581 | 1.387 | 0.000 | 0.068 | 60.2 | 2.582 |
| 11 | 0.006 | 0.000 | 0.003 | 0.000 | 0.003 | 0.809 | 0.054 | 0.020 | 0.025 | 0.124 | 0.101 | 0.184 | 0.501 | 1.138 | 0.074 | 0.130 | 26.2 | 2.027 |
| 12 | 0.004 | 0.000 | 0.003 | 0.000 | 0.005 | 0.692 | 0.065 | 0.031 | 0.020 | 0.122 | 0.107 | 0.186 | 0.484 | 1.109 | 0.065 | 0.115 | 42.3 | 1.959 |
| 13 | 0.006 | 0.010 | 0.003 | 0.000 | 0.015 | 0.403 | 1.049 | 0.445 | 0.000 | 0.000 | 0.000 | 0.292 | 0.144 | 0.260 | 0.000 | 0.000 | 36.1 | 0.695 |
| 14 | 0.005 | 0.002 | 0.002 | 0.000 | 0.026 | 0.594 | 0.363 | 0.193 | 0.000 | 0.000 | 0.000 | 0.403 | 0.216 | 0.545 | 0.000 | 0.000 | 69.2 | 1.165 |
| 15 | 0.008 | 0.002 | 0.003 | 0.000 | 0.027 | 1.171 | 1.128 | 0.196 | 0.000 | 0.000 | 0.000 | 1.749 | 1.080 | 1.891 | 0.000 | 0.101 | 61.8 | 4.821 |
| 16 | 0.006 | 0.000 | 0.004 | 0.000 | 0.005 | 0.880 | 0.064 | 0.022 | 0.030 | 0.162 | 0.142 | 0.286 | 0.633 | 1.469 | 0.088 | 0.141 | 30.5 | 2.617 |
| 17 | 0.015 | 0.000 | 0.009 | 0.000 | 0.016 | 2.291 | 0.190 | 0.064 | 0.065 | 0.322 | 0.220 | 0.440 | 1.307 | 3.073 | 0.205 | 0.381 | 40.4 | 5.406 |
| 18 | 0.008 | 0.000 | 0.004 | 0.000 | 0.003 | 1.684 | 0.157 | 0.031 | 0.045 | 0.155 | 0.168 | 0.543 | 1.149 | 2.038 | 0.131 | 0.238 | 22.3 | 4.099 |
| 19 | 0.005 | 0.000 | 0.003 | 0.000 | 0.007 | 0.712 | 0.074 | 0.026 | 0.000 | 0.000 | 0.000 | 0.558 | 0.346 | 0.816 | 0.000 | 0.067 | 48.0 | 1.788 |
| 20 | 0.005 | 0.000 | 0.003 | 0.000 | 0.007 | 0.774 | 0.080 | 0.027 | 0.000 | 0.000 | 0.000 | 0.479 | 0.356 | 0.848 | 0.000 | 0.068 | 47.5 | 1.751 |
| 21 | 0.005 | 0.000 | 0.003 | 0.000 | 0.009 | 0.614 | 0.054 | 0.000 | 0.000 | 0.000 | 0.000 | 0.427 | 0.294 | 0.699 | 0.000 | 0.056 | 51.1 | 1.477 |
| 22 | 0.005 | 0.000 | 0.005 | 0.000 | 0.013 | 1.117 | 0.179 | 0.075 | 0.000 | 0.000 | 0.000 | 0.481 | 0.414 | 1.023 | 0.000 | 0.063 | 57.5 | 1.981 |
| 23 | 0.007 | 0.000 | 0.006 | 0.000 | 0.019 | 1.374 | 0.257 | 0.102 | 0.000 | 0.000 | 0.000 | 0.551 | 0.478 | 1.178 | 0.000 | 0.068 | 59.9 | 2.275 |
| 24 | 0.006 | 0.000 | 0.004 | 0.000 | 0.014 | 1.181 | 0.228 | 0.082 | 0.000 | 0.000 | 0.000 | 0.433 | 0.403 | 0.984 | 0.000 | 0.057 | 58.9 | 1.877 |
| 25 | 0.010 | 0.000 | 0.005 | 0.000 | 0.011 | 0.641 | 0.096 | 0.019 | 0.000 | 0.000 | 0.000 | 1.121 | 0.642 | 1.207 | 0.000 | 0.122 | 42.6 | 3.092 |
| 26 | 0.008 | 0.000 | 0.005 | 0.000 | 0.013 | 1.270 | 0.149 | 0.066 | 0.000 | 0.000 | 0.000 | 1.751 | 1.287 | 1.468 | 0.000 | 0.143 | 50.8 | 4.649 |
| 27 | 0.020 | 0.000 | 0.009 | 0.000 | 0.040 | 0.471 | 0.095 | 0.000 | 0.000 | 0.000 | 0.000 | 1.635 | 1.750 | 2.498 | 0.000 | 0.176 | 57.9 | 6.059 |
| 28 | 0.021 | 0.000 | 0.010 | 0.000 | 0.027 | 0.947 | 0.259 | 0.060 | 0.000 | 0.000 | 0.000 | 1.081 | 0.848 | 1.753 | 0.000 | 0.128 | 46.7 | 3.810 |
| 29 | 0.018 | 0.002 | 0.009 | 0.000 | 0.009 | 0.589 | 0.079 | 0.017 | 0.000 | 0.065 | 0.060 | 0.567 | 0.640 | 1.344 | 0.000 | 0.155 | 23.2 | 2.706 |
| 30 | 0.010 | 0.000 | 0.005 | 0.000 | 0.011 | 1.521 | 0.330 | 0.148 | 0.020 | 0.014 | 0.032 | 1.055 | 0.877 | 1.639 | 0.000 | 0.124 | 41.9 | 3.694 |
| 31 | 0.008 | 0.000 | 0.005 | 0.000 | 0.014 | 2.170 | 0.595 | 0.163 | 0.000 | 0.000 | 0.000 | 1.406 | 1.255 | 2.150 | 0.000 | 0.157 | 51.5 | 4.969 |
| 32 | 0.006 | 0.000 | 0.003 | 0.000 | 0.009 | 1.998 | 0.519 | 0.142 | 0.000 | 0.000 | 0.000 | 1.156 | 1.098 | 1.854 | 0.068 | 0.143 | 49.6 | 4.318 |

TABLE 5-continued

| Plant | Anthocyanidin (mg/g fresh weight) | | | | Flavonol (mg/g fresh weight) | | | | Flavone (mg/g fresh weight) | | | | Flavone C-glycoside (mg/g fresh weight) | | | | Mal | Total flavone C-glycosides (mg/g fresh weight) |
|---|---|---|---|---|---|---|---|---|---|---|---|---|---|---|---|---|---|---|
| No. | Del | Cya | Pet | Pel | Mal | M | Q | K | Tri | Lut | Api | Vic2 | VX | IVX | Ori | Iori | (%) | weight |
| Average | | | | | | | | | | | | | | | | | 43.9 | 3.002 |
| S.D. | | | | | | | | | | | | | | | | | 14.4 | 1.329 |

Host: Ocean Song
Del: delphinidin,
Cya: cyanidin,
Pet: petunidin,
Pel: pelargonidin,
Mal: malvidin
M: myricetin,
Q: quercetin,
K: kaempferol
Tri: tricetin,
Lut: luteolin,
Api: apigenin,
Vic2: vicenin-2,
VX: vitexin,
IVX: isovitexin,
Ori: orientin,
Iori: isoorientin
Mal(%): Proportion of malvidin in total anthocyanidins Example 6: Transfer of *Campanula*-Derived F3',5'H Gene, Torenia-Derived MT Gene, Licorice-Derived F2H Gene, Buckwheat-Derived Codon Usage-Modified CGT Gene and *Lotus japonicus*-Derived FDH Gene into Rose Variety "Ocean Song"

Plasmid pSPB7809 has pBINPLUS as the basic backbone, and contains the following four expression cassettes.

(1) El$_2$35S promoter, *Campanula*-derived F3',5'H full-length cDNA (SEQ ID NO: 1) and D8 terminator (2) El$_2$35S promoter, torenia-derived MT full-length cDNA (SEQ ID NO: 3) and *Arabidopsis thaliana*-derived HSP terminator (3) El$_2$35S promoter, licorice-derived F2H full-length cDNA (SEQ ID NO: 5) and *perilla*-derived AT terminator (4) El$_2$35S promoter, buckwheat-derived codon usage-modified CGT full-length cDNA (SEQ ID NO: 11) (*Arabidopsis thaliana* alcohol dehydrogenase (ADH) gene-derived 5'-UTR (SEQ ID NO: 15) added to the 5'-position end) and *Arabidopsis thaliana*-derived HSP terminator (5) El$_2$35S promoter, *Lotus japonicus*-derived FDH full-length cDNA (SEQ ID NO: 9) and *Arabidopsis thaliana*-derived HSP terminator This plasmid constitutively expresses the *Campanula* F3',5'H gene, torenia MT gene, licorice F2H gene, buckwheat codon usage-modified CGT gene and *Lotus japonicus* FDH gene in plants.

The constructed plasmid pSPB7809 was introduced into the blue rose variety "Ocean Song", and a total of 143 transformants were obtained. The flavone C-glycosides isovitexin (apigenin 6-C-glucoside), vitexin (apigenin 8-C-glucoside), isoorientin (luteolin 6-C-glucoside), orientin (luteolin 8-C-glucoside) and vicenin-2 (apigenin 6,8-di-C-glucoside), and the anthocyanidins delphinidin, cyanidin, petunidin, pelargonidin and malvidin, were then identified and quantified. As a result, accumulation of flavone C-glycosides was confirmed in 58 transformants. The mean content of flavone C-glycosides was 3.24 mg per 1 g of fresh petal weight, with the flavone 6-C-glycoside isovitexin detected as the main component. The malvidin content was a maximum of 80.3% (average: 46.6%).

Thus, the average content of flavone C-glycosides per 1 g of fresh petal weight was higher in the OS/7809 line described in the Examples. Similar to the results obtained in Examples 3 and 4, it was shown to be possible to produce flavone C-glycosides more efficiently with the codon-modified CGT gene than with the original buckwheat-derived CGT gene.

The measured values for representative transformants are shown in Table 6 below.

TABLE 6

| Plant | Anthocyanidin (mg/g fresh weight) | | | | Flavonol (mg/g fresh weight) | | | | Flavone (mg/g fresh weight) | | | | Flavone C-glycoside (mg/g fresh weight) | | | | Mal | Total flavone C-glycosides (mg/g fresh weight) |
|---|---|---|---|---|---|---|---|---|---|---|---|---|---|---|---|---|---|---|
| No. | Del | Cya | Pet | Pel | Mal | M | Q | K | Tri | Lut | Api | Vic2 | VX | IVX | Ori | Iori | (%) | weight |
| Host | 0.000 | 0.024 | 0.000 | 0.000 | 0.000 | 0.000 | 2.883 | 0.586 | 0.000 | 0.000 | 0.000 | 0.000 | 0.000 | 0.000 | 0.000 | 0.000 | — | — |
| 1 | 0.019 | 0.000 | 0.003 | 0.000 | 0.002 | 0.576 | 0.068 | 0.020 | 0.083 | 0.137 | 0.071 | 0.445 | 1.009 | 2.121 | 0.136 | 0.280 | 7.0 | 3.991 |
| 2 | 0.011 | 0.000 | 0.005 | 0.000 | 0.033 | 0.865 | 0.091 | 0.042 | 0.000 | 0.000 | 0.000 | 1.133 | 0.673 | 1.375 | 0.047 | 0.106 | 67.1 | 3.335 |
| 3 | 0.011 | 0.000 | 0.005 | 0.000 | 0.028 | 1.183 | 0.119 | 0.068 | 0.000 | 0.000 | 0.000 | 0.954 | 0.602 | 1.284 | 0.053 | 0.096 | 63.9 | 2.988 |
| 4 | 0.009 | 0.000 | 0.005 | 0.000 | 0.017 | 1.332 | 0.177 | 0.093 | 0.000 | 0.000 | 0.000 | 0.942 | 0.498 | 1.150 | 0.041 | 0.089 | 54.4 | 2.720 |
| 5 | 0.015 | 0.000 | 0.007 | 0.000 | 0.018 | 1.521 | 0.209 | 0.107 | 0.000 | 0.000 | 0.000 | 1.223 | 0.748 | 1.707 | 0.062 | 0.139 | 45.8 | 3.879 |

TABLE 6-continued

| Plant No. | Anthocyanidin (mg/g fresh weight) | | | | Flavonol (mg/g fresh weight) | | | | Flavone (mg/g fresh weight) | | | | Flavone C-glycoside (mg/g fresh weight) | | | | Mal (%) | Total flavone C-glycosides (mg/g fresh weight) |
|---|---|---|---|---|---|---|---|---|---|---|---|---|---|---|---|---|---|---|
| | Del | Cya | Pet | Pel | Mal | M | Q | K | Tri | Lut | Api | Vic2 | VX | IVX | Ori | Iori | | |
| 6 | 0.013 | 0.000 | 0.007 | 0.000 | 0.017 | 1.007 | 0.131 | 0.064 | 0.000 | 0.000 | 0.000 | 0.844 | 0.523 | 1.181 | 0.047 | 0.101 | 46.1 | 2.694 |
| 7 | 0.017 | 0.000 | 0.006 | 0.000 | 0.018 | 1.852 | 0.363 | 0.200 | 0.000 | 0.000 | 0.000 | 0.759 | 0.711 | 1.482 | 0.042 | 0.091 | 44.5 | 3.083 |
| 8 | 0.009 | 0.000 | 0.006 | 0.000 | 0.018 | 1.395 | 0.253 | 0.130 | 0.000 | 0.000 | 0.000 | 0.819 | 0.819 | 1.790 | 0.052 | 0.113 | 53.2 | 3.593 |
| 9 | 0.007 | 0.000 | 0.002 | 0.000 | 0.006 | 0.694 | 0.000 | 0.000 | 0.057 | 0.254 | 0.122 | 0.381 | 0.470 | 1.075 | 0.105 | 0.187 | 38.8 | 2.219 |
| 10 | 0.011 | 0.000 | 0.003 | 0.000 | 0.003 | 0.711 | 0.000 | 0.000 | 0.062 | 0.222 | 0.099 | 0.365 | 0.533 | 1.243 | 0.117 | 0.214 | 18.9 | 2.472 |
| 11 | 0.010 | 0.000 | 0.005 | 0.000 | 0.007 | 0.772 | 0.000 | 0.000 | 0.023 | 0.104 | 0.090 | 0.481 | 0.451 | 1.070 | 0.062 | 0.122 | 32.1 | 2.186 |
| 12 | 0.009 | 0.000 | 0.005 | 0.000 | 0.012 | 1.093 | 0.121 | 0.066 | 0.000 | 0.000 | 0.000 | 0.618 | 0.508 | 1.105 | 0.051 | 0.078 | 47.4 | 2.360 |
| 13 | 0.006 | 0.000 | 0.004 | 0.000 | 0.008 | 0.858 | 0.070 | 0.027 | 0.000 | 0.000 | 0.000 | 1.033 | 0.874 | 1.896 | 0.071 | 0.163 | 44.1 | 4.038 |
| 14 | 0.035 | 0.003 | 0.005 | 0.000 | 0.003 | 1.213 | 0.803 | 0.673 | 0.000 | 0.000 | 0.000 | 0.599 | 0.064 | 0.263 | 0.000 | 0.000 | 5.7 | 0.926 |
| 15 | 0.011 | 0.000 | 0.003 | 0.000 | 0.002 | 0.921 | 0.000 | 0.000 | 0.066 | 0.243 | 0.117 | 0.387 | 0.685 | 1.543 | 0.129 | 0.218 | 15.2 | 2.962 |
| 16 | 0.005 | 0.000 | 0.003 | 0.000 | 0.011 | 0.540 | 0.087 | 0.075 | 0.000 | 0.000 | 0.000 | 0.841 | 0.569 | 1.286 | 0.000 | 0.085 | 58.1 | 2.781 |
| 17 | 0.004 | 0.000 | 0.002 | 0.000 | 0.007 | 0.878 | 0.000 | 0.025 | 0.044 | 0.202 | 0.135 | 0.451 | 0.619 | 1.438 | 0.114 | 0.198 | 53.0 | 2.820 |
| 18 | 0.004 | 0.000 | 0.003 | 0.000 | 0.019 | 1.616 | 0.106 | 0.000 | 0.000 | 0.000 | 0.000 | 0.722 | 0.515 | 1.201 | 0.043 | 0.115 | 73.7 | 2.595 |
| 19 | 0.007 | 0.000 | 0.005 | 0.000 | 0.043 | 2.309 | 0.235 | 0.097 | 0.000 | 0.000 | 0.000 | 0.655 | 0.625 | 1.409 | 0.000 | 0.097 | 77.2 | 2.786 |
| 20 | 0.016 | 0.000 | 0.005 | 0.000 | 0.009 | 0.771 | 0.079 | 0.035 | 0.056 | 0.155 | 0.119 | 0.532 | 0.812 | 1.796 | 0.100 | 0.193 | 30.2 | 3.433 |
| 21 | 0.016 | 0.000 | 0.008 | 0.000 | 0.011 | 0.788 | 0.061 | 0.027 | 0.062 | 0.123 | 0.081 | 0.749 | 1.191 | 2.623 | 0.126 | 0.262 | 32.0 | 4.951 |
| 22 | 0.010 | 0.000 | 0.005 | 0.000 | 0.007 | 0.884 | 0.055 | 0.000 | 0.030 | 0.116 | 0.085 | 0.514 | 0.679 | 1.530 | 0.085 | 0.156 | 32.8 | 2.964 |
| 23 | 0.006 | 0.000 | 0.003 | 0.000 | 0.031 | 0.947 | 0.171 | 0.082 | 0.000 | 0.000 | 0.000 | 1.412 | 0.844 | 2.030 | 0.058 | 0.113 | 76.8 | 4.457 |
| 24 | 0.011 | 0.000 | 0.004 | 0.000 | 0.028 | 1.048 | 0.173 | 0.091 | 0.000 | 0.000 | 0.000 | 0.959 | 0.608 | 1.396 | 0.048 | 0.102 | 65.0 | 3.113 |
| 25 | 0.015 | 0.000 | 0.003 | 0.000 | 0.005 | 1.028 | 0.000 | 0.000 | 0.050 | 0.134 | 0.071 | 0.336 | 0.997 | 1.946 | 0.139 | 0.245 | 21.8 | 3.664 |
| 26 | 0.006 | 0.000 | 0.004 | 0.000 | 0.010 | 0.443 | 0.000 | 0.000 | 0.165 | 0.397 | 0.114 | 0.330 | 0.000 | 0.418 | 0.045 | 0.110 | 49.1 | 0.903 |
| 27 | 0.005 | 0.000 | 0.003 | 0.000 | 0.008 | 0.513 | 0.000 | 0.000 | 0.124 | 0.604 | 0.259 | 0.267 | 0.157 | 0.397 | 0.040 | 0.074 | 47.5 | 0.935 |
| 28 | 0.007 | 0.000 | 0.004 | 0.000 | 0.012 | 0.363 | 0.000 | 0.000 | 0.092 | 0.327 | 0.104 | 0.207 | 0.103 | 0.291 | 0.000 | 0.066 | 51.5 | 0.667 |
| 29 | 0.015 | 0.000 | 0.011 | 0.000 | 0.026 | 1.208 | 0.161 | 0.059 | 0.000 | 0.000 | 0.000 | 1.856 | 0.926 | 2.140 | 0.079 | 0.229 | 49.6 | 5.229 |
| 30 | 0.013 | 0.000 | 0.009 | 0.000 | 0.020 | 1.138 | 0.097 | 0.039 | 0.000 | 0.000 | 0.000 | 1.499 | 0.819 | 1.941 | 0.070 | 0.198 | 47.5 | 4.526 |
| 31 | 0.008 | 0.000 | 0.004 | 0.000 | 0.007 | 1.354 | 0.112 | 0.036 | 0.019 | 0.093 | 0.090 | 0.395 | 0.752 | 1.661 | 0.089 | 0.154 | 35.0 | 3.051 |
| 32 | 0.005 | 0.000 | 0.003 | 0.000 | 0.009 | 1.819 | 0.287 | 0.181 | 0.000 | 0.000 | 0.000 | 1.436 | 1.025 | 2.410 | 0.064 | 0.194 | 52.6 | 5.128 |
| 33 | 0.007 | 0.000 | 0.005 | 0.000 | 0.012 | 1.233 | 0.148 | 0.072 | 0.000 | 0.000 | 0.000 | 0.975 | 0.604 | 1.441 | 0.055 | 0.109 | 51.4 | 3.185 |
| 34 | 0.005 | 0.000 | 0.003 | 0.000 | 0.011 | 2.099 | 0.333 | 0.154 | 0.000 | 0.000 | 0.000 | 1.263 | 0.733 | 1.737 | 0.056 | 0.116 | 57.4 | 3.905 |
| 35 | 0.014 | 0.000 | 0.009 | 0.000 | 0.024 | 1.248 | 0.283 | 0.131 | 0.000 | 0.000 | 0.000 | 1.183 | 0.760 | 1.884 | 0.043 | 0.146 | 51.2 | 4.016 |
| 36 | 0.014 | 0.000 | 0.003 | 0.000 | 0.002 | 0.375 | 0.034 | 0.000 | 0.033 | 0.092 | 0.049 | 0.350 | 0.479 | 1.099 | 0.079 | 0.134 | 10.6 | 2.142 |
| 37 | 0.010 | 0.000 | 0.002 | 0.000 | 0.001 | 0.705 | 0.077 | 0.021 | 0.031 | 0.068 | 0.056 | 0.426 | 0.620 | 1.405 | 0.075 | 0.135 | 9.3 | 2.660 |
| 38 | 0.003 | 0.000 | 0.002 | 0.000 | 0.017 | 1.087 | 0.153 | 0.066 | 0.000 | 0.000 | 0.000 | 1.481 | 0.744 | 1.612 | 0.050 | 0.109 | 80.3 | 3.995 |
| 39 | 0.001 | 0.000 | 0.000 | 0.000 | 0.004 | 0.988 | 0.469 | 0.204 | 0.000 | 0.000 | 0.000 | 0.805 | 0.661 | 1.547 | 0.043 | 0.073 | 72.8 | 3.128 |
| 40 | 0.003 | 0.003 | 0.002 | 0.000 | 0.011 | 0.992 | 1.325 | 0.414 | 0.000 | 0.000 | 0.000 | 1.271 | 0.853 | 1.871 | 0.047 | 0.097 | 51.4 | 4.140 |
| 41 | 0.006 | 0.000 | 0.002 | 0.000 | 0.017 | 1.430 | 0.621 | 0.293 | 0.000 | 0.000 | 0.000 | 0.812 | 0.741 | 1.633 | 0.053 | 0.087 | 68.3 | 3.325 |
| 42 | 0.004 | 0.000 | 0.002 | 0.000 | 0.014 | 1.223 | 0.356 | 0.195 | 0.000 | 0.000 | 0.000 | 0.981 | 0.861 | 1.781 | 0.000 | 0.076 | 70.9 | 3.699 |
| 43 | 0.008 | 0.000 | 0.004 | 0.000 | 0.023 | 1.211 | 0.512 | 0.350 | 0.000 | 0.000 | 0.000 | 1.026 | 0.935 | 2.040 | 0.000 | 0.081 | 66.6 | 4.081 |
| 44 | 0.009 | 0.000 | 0.005 | 0.000 | 0.008 | 1.333 | 0.147 | 0.037 | 0.053 | 0.203 | 0.088 | 0.187 | 0.337 | 0.796 | 0.079 | 0.139 | 36.4 | 1.537 |
| 45 | 0.020 | 0.001 | 0.011 | 0.000 | 0.016 | 1.182 | 0.000 | 0.022 | 0.093 | 0.348 | 0.140 | 0.255 | 0.349 | 0.777 | 0.084 | 0.163 | 32.9 | 1.629 |
| 46 | 0.016 | 0.000 | 0.009 | 0.000 | 0.016 | 1.232 | 0.125 | 0.038 | 0.074 | 0.289 | 0.114 | 0.160 | 0.390 | 0.844 | 0.088 | 0.159 | 39.2 | 1.641 |
| 47 | 0.004 | 0.000 | 0.003 | 0.000 | 0.005 | 0.824 | 0.057 | 0.000 | 0.033 | 0.090 | 0.088 | 0.555 | 1.502 | 3.439 | 0.152 | 0.276 | 42.9 | 5.924 |
| 48 | 0.007 | 0.000 | 0.005 | 0.000 | 0.016 | 1.366 | 0.349 | 0.123 | 0.000 | 0.000 | 0.000 | 0.672 | 0.682 | 1.510 | 0.000 | 0.086 | 56.4 | 2.951 |
| 49 | 0.009 | 0.000 | 0.005 | 0.000 | 0.017 | 1.407 | 0.382 | 0.138 | 0.000 | 0.000 | 0.000 | 0.594 | 0.654 | 1.456 | 0.039 | 0.084 | 55.1 | 2.828 |
| 50 | 0.006 | 0.000 | 0.003 | 0.000 | 0.033 | 2.879 | 0.358 | 0.065 | 0.000 | 0.000 | 0.000 | 1.522 | 0.782 | 1.397 | 0.000 | 0.135 | 77.9 | 3.836 |
| 51 | 0.018 | 0.000 | 0.008 | 0.000 | 0.020 | 0.765 | 0.147 | 0.027 | 0.000 | 0.000 | 0.000 | 1.224 | 0.584 | 1.174 | 0.000 | 0.108 | 43.7 | 3.090 |
| 52 | 0.021 | 0.000 | 0.010 | 0.000 | 0.027 | 1.359 | 0.357 | 0.183 | 0.000 | 0.000 | 0.000 | 2.105 | 0.689 | 1.831 | 0.000 | 0.109 | 46.5 | 4.734 |
| 53 | 0.009 | 0.000 | 0.006 | 0.000 | 0.016 | 1.485 | 0.248 | 0.073 | 0.000 | 0.000 | 0.000 | 1.808 | 0.630 | 1.256 | 0.000 | 0.113 | 52.7 | 3.807 |
| 54 | 0.005 | 0.000 | 0.003 | 0.000 | 0.018 | 1.235 | 0.610 | 0.220 | 0.000 | 0.000 | 0.000 | 1.640 | 1.201 | 1.893 | 0.000 | 0.084 | 68.3 | 4.818 |
| 55 | 0.007 | 0.000 | 0.004 | 0.000 | 0.006 | 1.082 | 0.086 | 0.019 | 0.034 | 0.076 | 0.096 | 0.569 | 1.517 | 2.754 | 0.133 | 0.262 | 34.9 | 5.234 |
| 56 | 0.008 | 0.000 | 0.003 | 0.000 | 0.002 | 0.998 | 0.000 | 0.000 | 0.072 | 0.253 | 0.166 | 0.457 | 0.667 | 1.062 | 0.092 | 0.183 | 18.7 | 2.461 |
| 57 | 0.017 | 0.000 | 0.005 | 0.000 | 0.006 | 1.031 | 0.000 | 0.000 | 0.078 | 0.120 | 0.064 | 0.543 | 1.090 | 1.621 | 0.151 | 0.286 | 21.9 | 3.691 |
| 58 | 0.010 | 0.000 | 0.006 | 0.000 | 0.014 | 1.598 | 0.292 | 0.111 | 0.000 | 0.000 | 0.000 | 1.511 | 0.931 | 1.176 | 0.000 | 0.098 | 46.7 | 3.717 |

TABLE 6-continued

| Plant No. | Anthocyanidin (mg/g fresh weight) | | | | Flavonol (mg/g fresh weight) | | | | Flavone (mg/g fresh weight) | | | | Flavone C-glycoside (mg/g fresh weight) | | | | Mal (%) | Total flavone C-glycosides (mg/g fresh weight) |
|---|---|---|---|---|---|---|---|---|---|---|---|---|---|---|---|---|---|---|
| | Del | Cya | Pet | Pel | Mal | M | Q | K | Tri | Lut | Api | Vic2 | VX | IVX | Ori | Iori | | |
| Average | | | | | | | | | | | | | | | | | 46.6 | 3.235 |
| S.D. | | | | | | | | | | | | | | | | | 18.9 | 1.143 |

Host: Ocean Song
Del: delphinidin,
Cya: cyanidin,
Pet: petunidin,
Pel: pelargonidin,
Mal: malvidin
M: myricetin,
Q: quercetin,
K: kaempferol
Tri: tricetin,
Lut: luteolin,
Api: apigenin,
Vic2: vicenin-2,
VX: vitexin,
IVX: isovitexin,
Ori: orientin,
Iori: isoorientin
Mal(%): Proportion of malvidin in total anthocyanidins

Example 7: Evaluation of Flower Color of Flavone C-Glycoside-Containing Roses The transformants created in Examples 2 and 3 (with "Ocean Song" rose variety as host) were measured to determine the color shades of the respective petals using a CM-2022 spectrocolorimeter (Minolta) with a 10° visual field and a D65 light source, and analyzing with Spectra-Magic™ color management software (Minolta).

In comparing the average values of the hue angles, no differences in petal hue angle were found between the roses with buckwheat-derived (Example 3) and roses with rice-derived (Example 2) CGT genes. On the individual level, however, more transformants exhibited a hue angle of 315° or smaller among the roses with the transferred buckwheat-derived CGT gene, with one having been altered to the bluest color yet obtained, having a value of 294.5°. These results confirmed that using the buckwheat-derived CGT gene significantly increased the amount of flavone C-glycoside production, and especially the amount of mono-C-glycoside production, altering the petals to a blue color shade by their copresence with anthocyanins.

The results are shown in Table 7.

TABLE 7

| | Gene and flavonoid composition | Hue angle (hue) |
|---|---|---|
| Host | Ocean Song Stores cyanidin as main pigment, contains absolutely no flavone C-glycoside | Average: 362.57° |
| | (1) Campanula F3',5'H Has high storage of delphinidin as main pigment, contains absolutely no flavone C-glycoside | Average: 337.33°, bluest point: 333.15° |
| Example 2 | (2) Campanula F3',5'H + torenia MT + licorice F2H + rice CGT (codon usage modified) + Lotus japonicus FDH Has high storage of malvidin as main pigment, contains flavone C-glycoside | Average: 320.16°, bluest point: 318.89° |
| Example 3 | (3) Campanula F3',5'H + torenia MT + licorice F2H + buckwheat CGT (codon usage modified) + Lotus japonicus FDH Has high storage of delphinidin as main pigment, contains flavone C-glycoside | Average: 320.19°, bluest point: 294.53° |

SEQUENCE LISTING

The invention claimed is:

1. A buckwheat-derived C-glucosyltransferase (CGT) gene or its homolog, wherein:
the buckwheat-derived CGT gene or its homolog is a polynucleotide consisting of the nucleotide sequence as set forth in SEQ ID NO: 11.

2. The buckwheat-derived CGT gene or its homolog according to claim 1, wherein the *Arabidopsis thaliana* alcohol dehydrogenase (ADH) gene-derived untranslated region (5'-UTR) (SEQ ID NO: 15) or the *Arabidopsis thaliana* HSPRO gene-derived untranslated region (5'-UTR) (SEQ ID NO: 13) has been added.

3. A vector comprising a buckwheat-derived CGT gene or its homolog, wherein the buckwheat-derived CGT gene or its homolog is selected from the group consisting of:
(a) a polynucleotide consisting of the nucleotide sequence as set forth in SEQ ID NO: 11;
(b) a polynucleotide that encodes a protein consisting of the amino acid sequence as set forth in SEQ ID NO: 12; and
(c) a polynucleotide that encodes a protein having an amino acid sequence with at least 98% identity with respect to the amino acid sequence as set forth in SEQ ID NO: 12 and having the same activity as a protein encoded by the polynucleotide of (b), and
wherein the vector further comprises a flavanone 2-hydroxylase (F2H) gene or its homolog, and a dehydratase (FDH) gene or its homolog.

4. The vector according to claim 3, wherein the *Arabidopsis thaliana* ADH gene-derived untranslated region (5'-UTR) (SEQ ID NO: 15) or the *Arabidopsis thaliana* HSPRO gene-derived untranslated region (5'-UTR) (SEQ ID NO: 13) has been added to the buckwheat-derived CGT gene or its homolog.

5. The vector according to claim 3, wherein
the F2H gene or its homolog is selected from the group consisting of:
(a) a polynucleotide consisting of the nucleotide sequence as set forth in SEQ ID NO: 5;

(b) a polynucleotide that encodes a protein consisting of the amino acid sequence as set forth in SEQ ID NO: 6; and (c) a polynucleotide that encodes a protein having an amino acid sequence with at least 98% identity with respect to the amino acid sequence as set forth in SEQ ID NO: 6 and having the same activity as a protein encoded by the polynucleotide of (b), and the FDH gene or its homolog is selected from the group consisting of:

(a) a polynucleotide consisting of the nucleotide sequence as set forth in SEQ ID NO: 9;

(b) a polynucleotide that encodes a protein consisting of the amino acid sequence as set forth in SEQ ID NO: 10; and (c) a polynucleotide that encodes a protein having an amino acid sequence with at least 98% identity with respect to the amino acid sequence as set forth in SEQ ID NO: 10 and having the same activity as a protein encoded by the polynucleotide of (3b).

6. A transgenic rose plant or its inbred or outbred progeny, a propagule thereof, a partial plant body thereof, a tissue or a cell of the transgenic rose plant thereof, a cut flower of the transgenic rose plant thereof comprising the buckwheat-derived CGT gene or its homolog according to claim 1.

7. The transgenic plant or its inbred or outbred progeny, a propagule thereof, a partial plant body thereof, a tissue or a cell of the transgenic rose plant thereof, a cut flower of the transgenic rose plant thereof according to claim 6, wherein the cut flower of the transgenic rose plant is a processed form selected from the group consisting of preserved, dried or resin sealed.

8. A method for creating transgenic rose plants with blue flower color, comprising a step of transferring the buckwheat-derived C-glucosyltransferase (CGT) gene according to claim 1 into a host rose plant to cause delphinidin-type anthocyanins and flavone mono-C-glycosides to coexist in the rose plant cells.

9. The method according to claim 8, wherein the flavone mono-C-glycoside is apigenin 6-C-glucoside, luteolin 6-C-glucoside, tricetin 6-C-glucoside, apigenin 8-C-glucoside, luteolin 8-C-glucoside or tricetin 8-C-glucoside, or a derivative thereof.

10. The method according to claim 8, wherein the delphinidin-type anthocyanin is selected from the group consisting of malvidins, delphinidins, petunidins and their combinations.

11. A method for creating transgenic rose plants with blue flower color, comprising a step of transferring the vector according to claim 3 into a host plant to cause delphinidin-type anthocyanins and flavone mono-C-glycosides to coexist in the plant cells.

* * * * *

SEQUENCE LISTING

<160> NUMBER OF SEQ ID NOS: 15

<210> SEQ ID NO 1
<211> LENGTH: 1927
<212> TYPE: DNA
<213> ORGANISM: Campanula medium

<400> SEQUENCE: 1

```
accaaatgag ctttgtaatt tgagattaat cataattgca tgctcaacta acattctgta      60
ttcatatatc catatgtatt ttgacctata gatattacat tacaccttga ggcctttata     120
tatagagagt gtatctactt cccttaatat caccttttca ttcaacaagt gaagccacca     180
```

```
tgtctataga catatccacc ctcttctatg aacttgttgc agcaatttca ctctacttag    240
ctacctactc tttcattcgt ttcctcttca aaccctctca ccaccaccac ctccctcccg    300
gcccaaccgg atggccgatc atcggagccc ttccactctt aggcaccatg ccacatgttt    360
ccttagccga catggccgtt aaatacggtc tataatgta cctaaaactt ggttcaaagg     420
gcaccgtcgt ggcctcaaat ccaaaagccg cccgagcctt cttgaaaacc catgatgcca    480
atttttctaa ccgtccgatt gatggggggc ctacctacct cgcgtataat gcacaagaca    540 tggttttttgc agaatatggc ccaaaatgga agcttttgcg aaagctatgt agcttgcaca   600
tgttaggccc gaaggcactc gaggattggg ctcatgtcaa agtttcagag gtcggtcata    660
tgctcaaaga aatgtacgag caatcgagta agtcagtgcc agtgccagtg gtggtgccag    720
agatgttaac ttatgccatg ctaatatga ttggacgaat catactcagc cgacgcccct    780 tgttatcac gagcaaatta gactcgtctg cttctgcttc tgcttctgtt agtgaattcc     840
aatatatggt tatggagctc atgaggatgg cagggttgtt caatattggt gatttcatac    900
catatattgc atggatggat ttgcaaggca ttcaacgtga tatgaaggtt atacagaaaa    960
agtttgatgt cttgttgaac aaaatgatca aggaacatac agaatccgct catgatcgca    1020
aagataatcc tgatttcctt gatattctta tggcggctac ccaagaaaac acggagggaa    1080
ttcagcttaa tcttgtaaat gttaaggcac ttcttttgga tttattcacg gcgggcacgg    1140
atacatcatc aagtgtgatc gaatgggcac tagccgaaat gttgaaccat cgacagatcc    1200
taaaccgggc ccacgaagaa atggaccaag tcattggcag aaacagaaga ctagaacaat    1260
ctgacatacc aaacttgcca tatttccaag ccatatgcaa agaaacattc cgaaaacacc    1320
cttccacgcc cttaaacctc ccaagaatct caacagaagc atgtgaagtg acggatttc     1380 acataccaaa aaacactaga ctaatagtga acatatgggc aataggggag gaccctaaag    1440
tgtgggaaaa tccattagat tttactccgg aacgtttctt gagtgaaaaa cacgcgaaaa    1500
ttgatccgcg aggtaatcat tttgagttaa tcccatttgg ggctggacga aggatatgtg    1560
caggggctag aatgggagcg gcctcggtcg agtacatatt aggtacattg gtgcactcat    1620
ttgattggaa attgcctgat ggagttgtgg aagttaatat ggaagagagc tttgggatcg    1680
cattgcaaaa aaaagtgcct cttctgctat tgttactcc aagattgcct ccaagttctt     1740
acactgtcta ggcaaatgct tatatatatg aataattgat tgagttgttt agttgtatga    1800
aagatttgag aaaataaatt attaggtttt gcaccattat gttgagatgg ttgttgttag    1860
tgttaaggaa gtcgattgta gtaataataa ttttatttttt ttcgaaaaaa aaaaaaaaa   1920 aaaaaaa                                                              1927
```

<210> SEQ ID NO 2
<211> LENGTH: 523
<212> TYPE: PRT
<213> ORGANISM: Campanula medium

<400> SEQUENCE: 2

```
Met Ser Ile Asp Ile Ser Thr Leu Phe Tyr Glu Leu Val Ala Ala Ile
1               5                   10                  15

Ser Leu Tyr Leu Ala Thr Tyr Ser Phe Ile Arg Phe Leu Phe Lys Pro
                20                  25                  30

Ser His His His Leu Pro Pro Gly Pro Thr Gly Trp Pro Ile Ile
            35                  40                  45

Gly Ala Leu Pro Leu Leu Gly Thr Met Pro His Val Ser Leu Ala Asp
        50                  55                  60
```

```
Met Ala Val Lys Tyr Gly Pro Ile Met Tyr Leu Lys Leu Gly Ser Lys
 65                  70                  75                  80

Gly Thr Val Val Ala Ser Asn Pro Lys Ala Arg Ala Phe Leu Lys
                 85                  90                  95

Thr His Asp Ala Asn Phe Ser Asn Arg Pro Ile Asp Gly Gly Pro Thr
             100                 105                 110

Tyr Leu Ala Tyr Asn Ala Gln Asp Met Val Phe Ala Glu Tyr Gly Pro
             115                 120                 125

Lys Trp Lys Leu Leu Arg Lys Leu Cys Ser Leu His Met Leu Gly Pro
             130                 135                 140

Lys Ala Leu Glu Asp Trp Ala His Val Lys Val Ser Glu Val Gly His
145                 150                 155                 160

Met Leu Lys Glu Met Tyr Glu Gln Ser Ser Lys Ser Val Pro Val Pro
                 165                 170                 175

Val Val Val Pro Glu Met Leu Thr Tyr Ala Met Ala Asn Met Ile Gly
             180                 185                 190

Arg Ile Ile Leu Ser Arg Arg Pro Phe Val Ile Thr Ser Lys Leu Asp
             195                 200                 205

Ser Ser Ala Ser Ala Ser Ala Ser Val Ser Glu Phe Gln Tyr Met Val
210                 215                 220

Met Glu Leu Met Arg Met Ala Gly Leu Phe Asn Ile Gly Asp Phe Ile
225                 230                 235                 240

Pro Tyr Ile Ala Trp Met Asp Leu Gln Gly Ile Gln Arg Asp Met Lys
                 245                 250                 255

Val Ile Gln Lys Lys Phe Asp Val Leu Leu Asn Lys Met Ile Lys Glu
             260                 265                 270

His Thr Glu Ser Ala His Asp Arg Lys Asp Asn Pro Asp Phe Leu Asp
             275                 280                 285

Ile Leu Met Ala Ala Thr Gln Glu Asn Thr Glu Gly Ile Gln Leu Asn
290                 295                 300

Leu Val Asn Val Lys Ala Leu Leu Leu Asp Leu Phe Thr Ala Gly Thr
305                 310                 315                 320

Asp Thr Ser Ser Ser Val Ile Glu Trp Ala Leu Ala Glu Met Leu Asn
                 325                 330                 335

His Arg Gln Ile Leu Asn Arg Ala His Glu Glu Met Asp Gln Val Ile
             340                 345                 350

Gly Arg Asn Arg Arg Leu Glu Gln Ser Asp Ile Pro Asn Leu Pro Tyr
             355                 360                 365

Phe Gln Ala Ile Cys Lys Glu Thr Phe Arg Lys His Pro Ser Thr Pro
             370                 375                 380

Leu Asn Leu Pro Arg Ile Ser Thr Glu Ala Cys Glu Val Asp Gly Phe
385                 390                 395                 400

His Ile Pro Lys Asn Thr Arg Leu Ile Val Asn Ile Trp Ala Ile Gly
                 405                 410                 415

Arg Asp Pro Lys Val Trp Glu Asn Pro Leu Asp Phe Thr Pro Glu Arg
             420                 425                 430

Phe Leu Ser Glu Lys His Ala Lys Ile Asp Pro Arg Gly Asn His Phe
             435                 440                 445

Glu Leu Ile Pro Phe Gly Ala Gly Arg Arg Ile Cys Ala Gly Ala Arg
             450                 455                 460

Met Gly Ala Ala Ser Val Glu Tyr Ile Leu Gly Thr Leu Val His Ser
465                 470                 475                 480
```

Phe Asp Trp Lys Leu Pro Asp Gly Val Val Glu Val Asn Met Glu Glu
                485                 490                 495

Ser Phe Gly Ile Ala Leu Gln Lys Lys Val Pro Leu Ser Ala Ile Val
            500                 505                 510

Thr Pro Arg Leu Pro Ser Ser Tyr Thr Val
        515                 520

<210> SEQ ID NO 3
<211> LENGTH: 720
<212> TYPE: DNA
<213> ORGANISM: Torenia hybrid cultivar

<400> SEQUENCE: 3

```
atgaaagata agttctatgg caccattttg cagagcgaag ccctcgcaaa gtatctgtta        60
gagacaagtg cctatccacg agaacatccg cagctcaaag aactaaggag cgcaactgtg       120
gacaagtatc aatattggag cttgatgaat gttccagctg atgagggca gttcatttca        180
atgttactga aaattatgaa cgcaaaaaag acaattgaag ttggagtttt cacaggctac       240
tcactcctat caactgctct ggctctacct gatgatggca aaatcgttgc cattgatcct       300
gatagagaag cttatgagac tggtttgcca tttatcaaga agcaaacgt ggctcataaa        360
atccaataca tacaatctga tgccatgaaa gtcatgaatg acctcattgc tgccaaggga       420
gaagaagaag aggggagctt tgactttggg ttcgtggatg cagacaaaga aaactacata       480
aactaccacg agaaactgtt gaagctggtt aaggttggag ggatcatagg atacgacaac       540
actctgtggt ctggaacagt tgctgcatct gaagacgatg agaataatat gcaagactac       600
ttaagaggtt gcagagggca tatcctcaaa ctaaactcct ttctcgcaaa cgatgatcgg       660
attgaattgg ctcacctctc tattggagat ggactcacct tgtgcaaacg tctcaaataa       720
```

<210> SEQ ID NO 4
<211> LENGTH: 239
<212> TYPE: PRT
<213> ORGANISM: Torenia hybrid cultivar

<400> SEQUENCE: 4

Met Lys Asp Lys Phe Tyr Gly Thr Ile Leu Gln Ser Glu Ala Leu Ala
1               5                   10                  15

Lys Tyr Leu Leu Glu Thr Ser Ala Tyr Pro Arg Glu His Pro Gln Leu
            20                  25                  30

Lys Glu Leu Arg Ser Ala Thr Val Asp Lys Tyr Gln Tyr Trp Ser Leu
        35                  40                  45

Met Asn Val Pro Ala Asp Glu Gly Gln Phe Ile Ser Met Leu Leu Lys
    50                  55                  60

Ile Met Asn Ala Lys Lys Thr Ile Glu Val Gly Val Phe Thr Gly Tyr
65                  70                  75                  80

Ser Leu Leu Ser Thr Ala Leu Ala Leu Pro Asp Asp Gly Lys Ile Val
                85                  90                  95

Ala Ile Asp Pro Asp Arg Glu Ala Tyr Glu Thr Gly Leu Pro Phe Ile
            100                 105                 110

Lys Lys Ala Asn Val Ala His Lys Ile Gln Tyr Ile Gln Ser Asp Ala
        115                 120                 125

Met Lys Val Met Asn Asp Leu Ile Ala Ala Lys Gly Glu Glu Glu Glu
    130                 135                 140

Gly Ser Phe Asp Phe Gly Phe Val Asp Ala Asp Lys Glu Asn Tyr Ile
145                 150                 155                 160

```
Asn Tyr His Glu Lys Leu Leu Lys Leu Val Lys Val Gly Gly Ile Ile
            165                 170                 175

Gly Tyr Asp Asn Thr Leu Trp Ser Gly Thr Val Ala Ala Ser Glu Asp
        180                 185                 190

Asp Glu Asn Asn Met Gln Asp Tyr Leu Arg Gly Cys Arg Gly His Ile
        195                 200                 205

Leu Lys Leu Asn Ser Phe Leu Ala Asn Asp Asp Arg Ile Glu Leu Ala
    210                 215                 220

His Leu Ser Ile Gly Asp Gly Leu Thr Leu Cys Lys Arg Leu Lys
225                 230                 235
```

<210> SEQ ID NO 5
<211> LENGTH: 1920
<212> TYPE: DNA
<213> ORGANISM: Glycyrrhiza echinata

<400> SEQUENCE: 5

```
ccccaatttc ctctatcata agccattccg ttgattgagc ttcctttccg tgaaaaaaat      60
aactaagcga tatggaacct caactcgtag cagtgtctgt gttggtttca gcacttatct    120
gctacttctt tttccggcca tatttccacc gttacgaaaa aaaccttcca ccatctcctt    180
ttttccggct tccaataatt ggccacatgc acatgttagg tccccttctt caccaatcct    240
tccacaacct ctcccaccgt tacggtcctc tgttttcact taactttggc tctgttctct    300
gtgtcgttgc ttcaaccect cactttgcca acaactcct tcaaaccaac gaactcgcct     360
ttaactgtcg cattgaatca accgccgtta aaaaactcac ttacgagtct tccttggcct    420
tcgcacctta cggtgattac tggaggttca ttaagaagct gagcatgaac gagcttttgg    480
gctctcgtag cataaacaac ttccaacacc tacgagcaca agagacccat caattgttaa    540
ggcttttgtc caacagggca agagcgtttg aggccgtgaa tatcaccgag gagcttctta    600
agttgaccaa caacgttatt ctataatga tggttgggga ggcagaggag gcaagggatg     660
tggtgcgtga tgtgacggag atatttggag agtttaatgt ttcggatttt atttggttgt    720
ttaagaagat ggacttgcag gggtttggga gaggattga ggatttgttt cagaggtttg     780
atacgttggt ggaaaggatt attagcaagc gggagcagac gaggaaagac agaaggagga    840
atgggaagaa gggtgagcag gggagtggtg atgggatcag agactttctt gatatcttgc    900
ttgactgtac tgaggatgag aattccgaga ttaaaatcca aagggttcac attaaggcct    960
tgattatgga tttcttcact gcagggacgg ataccacagc gatttcaaca gagtgggcat   1020
tagtggagct cgtcaagaaa ccctccgtgc tacaaaaagt tcgtgaagag atagacaatg   1080
tcgtaggaaa agacagactt gttgaggaat ctgattgtcc taatctccca tatctccaag   1140
ccattcttaa agaacattc cgtttgcacc caccggttcc tatggttaca agaagatgcg    1200
tggcagagtg cacggtagag aattacgtca tcccagaaga ctcacttctc tttgtgaatg   1260
tttggtccat cggaagaaac ccaaagtttt gggacaaccc attggagttt cgccccgaac   1320
gattcttaaa actagaagga gattccagtg gagttgttga tgtgagggga agccattttc   1380
agcttctgcc atttgggtct ggaaggagga tgtgccctgg tgtgtccttg gctatgcaag   1440
aggtgccagc actacttggt gctataatcc agtgctttga tttccacgtt gtgggtccca   1500
aaggtgagat tttgaagggt gatgacatag tcattaatgt ggatgaaagg ccaggattga   1560
cggctccaag ggcacataac cttgtgtgtg ttccgttga tagaacaagt ggcggtggac    1620
ccctcaaaat cattgaatgt tgattattcg tctcttgaat ttggatctgt gtgtggcttt   1680
```

-continued

```
gaataacatg tatggtgtat gtatgtatgt gttctttct ttctttctaa ttctgatcag    1740
tagcgtacac taggcactag ccttcgttag tggcaataac ttcggcaaat taacgaacat    1800
atgctgttca gagatatttt ttgccatgta tcgtcattct attctaggtt gttttttccgt   1860 tttccttatt acattctatg ataaatataa taaattgagt aatattatag tctcttaatt    1920
```

```
<210> SEQ ID NO 6
<211> LENGTH: 523
<212> TYPE: PRT
<213> ORGANISM: Glycyrrhiza echinata

<400> SEQUENCE: 6

Met Glu Pro Gln Leu Val Ala Val Ser Val Leu Val Ser Ala Leu Ile
1               5                   10                  15

Cys Tyr Phe Phe Phe Arg Pro Tyr Phe His Arg Tyr Gly Lys Asn Leu
                20                  25                  30

Pro Pro Ser Pro Phe Phe Arg Leu Pro Ile Ile Gly His Met His Met
            35                  40                  45

Leu Gly Pro Leu Leu His Gln Ser Phe His Asn Leu Ser His Arg Tyr
        50                  55                  60

Gly Pro Leu Phe Ser Leu Asn Phe Gly Ser Val Leu Cys Val Val Ala
65                  70                  75                  80

Ser Thr Pro His Phe Ala Lys Gln Leu Leu Gln Thr Asn Glu Leu Ala
                85                  90                  95

Phe Asn Cys Arg Ile Glu Ser Thr Ala Val Lys Lys Leu Thr Tyr Glu
                100                 105                 110

Ser Ser Leu Ala Phe Ala Pro Tyr Gly Asp Tyr Trp Arg Phe Ile Lys
            115                 120                 125

Lys Leu Ser Met Asn Glu Leu Leu Gly Ser Arg Ser Ile Asn Asn Phe
        130                 135                 140

Gln His Leu Arg Ala Gln Glu Thr His Gln Leu Leu Arg Leu Leu Ser
145                 150                 155                 160

Asn Arg Ala Arg Ala Phe Glu Ala Val Asn Ile Thr Glu Glu Leu Leu
                165                 170                 175

Lys Leu Thr Asn Asn Val Ile Ser Ile Met Met Val Gly Glu Ala Glu
            180                 185                 190

Glu Ala Arg Asp Val Val Arg Asp Val Thr Glu Ile Phe Gly Glu Phe
        195                 200                 205

Asn Val Ser Asp Phe Ile Trp Leu Phe Lys Lys Met Asp Leu Gln Gly
    210                 215                 220

Phe Gly Lys Arg Ile Glu Asp Leu Phe Gln Arg Phe Asp Thr Leu Val
225                 230                 235                 240

Glu Arg Ile Ile Ser Lys Arg Glu Gln Thr Arg Lys Asp Arg Arg
                245                 250                 255

Asn Gly Lys Lys Gly Glu Gln Gly Ser Gly Asp Gly Ile Arg Asp Phe
            260                 265                 270

Leu Asp Ile Leu Leu Asp Cys Thr Glu Asp Glu Asn Ser Glu Ile Lys
        275                 280                 285

Ile Gln Arg Val His Ile Lys Ala Leu Ile Met Asp Phe Phe Thr Ala
    290                 295                 300

Gly Thr Asp Thr Thr Ala Ile Ser Thr Glu Trp Ala Leu Val Glu Leu
305                 310                 315                 320

Val Lys Lys Pro Ser Val Leu Gln Lys Val Arg Glu Glu Ile Asp Asn
                325                 330                 335
```

```
Val Val Gly Lys Asp Arg Leu Val Glu Ser Asp Cys Pro Asn Leu
            340                 345                 350

Pro Tyr Leu Gln Ala Ile Leu Lys Glu Thr Phe Arg Leu His Pro Pro
        355                 360                 365

Val Pro Met Val Thr Arg Arg Cys Val Ala Glu Cys Thr Val Glu Asn
    370                 375                 380

Tyr Val Ile Pro Glu Asp Ser Leu Leu Phe Val Asn Val Trp Ser Ile
385                 390                 395                 400

Gly Arg Asn Pro Lys Phe Trp Asp Asn Pro Leu Glu Phe Arg Pro Glu
                405                 410                 415

Arg Phe Leu Lys Leu Glu Gly Asp Ser Ser Gly Val Val Asp Val Arg
            420                 425                 430

Gly Ser His Phe Gln Leu Leu Pro Phe Gly Ser Gly Arg Arg Met Cys
        435                 440                 445

Pro Gly Val Ser Leu Ala Met Gln Glu Val Pro Ala Leu Leu Gly Ala
    450                 455                 460

Ile Ile Gln Cys Phe Asp Phe His Val Val Gly Pro Lys Gly Glu Ile
465                 470                 475                 480

Leu Lys Gly Asp Asp Ile Val Ile Asn Val Asp Glu Arg Pro Gly Leu
                485                 490                 495

Thr Ala Pro Arg Ala His Asn Leu Val Cys Val Pro Val Asp Arg Thr
            500                 505                 510

Ser Gly Gly Gly Pro Leu Lys Ile Ile Glu Cys
        515                 520

<210> SEQ ID NO 7
<211> LENGTH: 1416
<212> TYPE: DNA
<213> ORGANISM: Oryza sativa Japonica Group

<400> SEQUENCE: 7
atgccgagct ctggcgacgc ggcgggcagg cggccgcatg tggtgctcat cccgagcgcc      60
ggcatgggcc acctcgtccc cttcggccgc ctcgccgtgg cgctctcctc cggccacggc     120
tgcgacgtct ccctcgtcac ggtgctcccc acggtgtcca ccgcggagtc gaagcacctc     180
gacgcgctgt cgacgcgttt cccggcggtg cggcggctcg acttcgagct cgcgccgttc     240
gacgcgtcgg agttcccccag cgccgacccg ttcttcctcc ggttcgaggc catgcggcgg     300
tcggcgccgc tgctcggccc gctcctcacc ggcgccggcg catcggcgct cgccacggac     360
atcgcgctga catccgtcgt catacccgtg gcgaaggagc agggcctccc cgtgccacatc    420 ctcttcaccg cctccgccgc gatgctctcc ctctgcgcct acttccccac ataccctcgac   480 gccaacgctg gcgacggcgg cggcgtcggc gacgtcgaca tccccggcgt gtaccgcatc     540
cccaaggcct ccatcccgca ggcgctgcac gatcccaacc acctcttcac ccgccagttc     600
gtcgccaacg gccggagcct cacgagcgcc gccggcatcc tcgtcaacac gttcgacgcc     660
ttggagccgg aggccgtcgc ggccctgcag cagggcaagg tcgcctccgg cttcccgccg     720
gtgttcgccg tggggccact tctcccggcg agcaaccagg caaagatcc gcaggcaaac      780 tacatggagt ggctcgacgc gcagccggcg cggtcggtgg tgtacgtgag cttcggcagc     840
cgcaaggcca tctcaggga gcagctcagg gagctcgccg ccgggctgga gaccagcggc      900
cacaggttcc tgtgggtggt gaagagcacc gtcgtggaca gggacgacgc cgccgagctc     960
ggcgagctgc tcggcgaggg gttcttgaag cgggtggaga gcgaggcct cgtcaccaag     1020 gcatgggtgg atcaggaaga ggtcctgaag cacgagtccg tggcgctgtt cgtgagccac    1080
```

```
tgcggctgga actcggtgac ggaggcggcg gcgagcggcg tcccggtgct ggcgctgccg    1140
aggttcggcg accagcgggt gaactccggc gtggtgcgc gcgccgggct cggcgtgtgg    1200
gcggacacct ggagctggga gggggaagcc ggggtgatcg gcgcagagga gatatcggag    1260
aaggtgaagg cggcgatggc ggacgaggcg ttgcgtagga aggcggcgag cctcgccaag    1320
gccgccgcga aggccgtcgc cggcggtgga tcgagccacc gttgtctggt cgagttcgcg    1380
cggctgtgcc aagggggaac atgtcgcact aattga                              1416
```

<210> SEQ ID NO 8
<211> LENGTH: 471
<212> TYPE: PRT
<213> ORGANISM: Oryza sativa Japonica Group

<400> SEQUENCE: 8

```
Met Pro Ser Ser Gly Asp Ala Ala Gly Arg Arg Pro His Val Val Leu
1               5                   10                  15

Ile Pro Ser Ala Gly Met Gly His Leu Val Pro Phe Gly Arg Leu Ala
                20                  25                  30

Val Ala Leu Ser Ser Gly His Gly Cys Asp Val Ser Leu Val Thr Val
            35                  40                  45

Leu Pro Thr Val Ser Thr Ala Glu Ser Lys His Leu Asp Ala Leu Phe
    50                  55                  60

Asp Ala Phe Pro Ala Val Arg Arg Leu Asp Phe Glu Leu Ala Pro Phe
65                  70                  75                  80

Asp Ala Ser Glu Phe Pro Ser Ala Asp Pro Phe Phe Leu Arg Phe Glu
                85                  90                  95

Ala Met Arg Arg Ser Ala Pro Leu Leu Gly Pro Leu Leu Thr Gly Ala
                100                 105                 110

Gly Ala Ser Ala Leu Ala Thr Asp Ile Ala Leu Thr Ser Val Val Ile
            115                 120                 125

Pro Val Ala Lys Glu Gln Gly Leu Pro Cys His Ile Leu Phe Thr Ala
    130                 135                 140

Ser Ala Ala Met Leu Ser Leu Cys Ala Tyr Phe Pro Thr Tyr Leu Asp
145                 150                 155                 160

Ala Asn Ala Gly Asp Gly Gly Val Gly Asp Val Asp Ile Pro Gly
                165                 170                 175

Val Tyr Arg Ile Pro Lys Ala Ser Ile Pro Gln Ala Leu His Asp Pro
            180                 185                 190

Asn His Leu Phe Thr Arg Gln Phe Val Ala Asn Gly Arg Ser Leu Thr
    195                 200                 205

Ser Ala Ala Gly Ile Leu Val Asn Thr Phe Asp Ala Leu Glu Pro Glu
210                 215                 220

Ala Val Ala Ala Leu Gln Gln Gly Lys Val Ala Ser Gly Phe Pro Pro
225                 230                 235                 240

Val Phe Ala Val Gly Pro Leu Leu Pro Ala Ser Asn Gln Ala Lys Asp
                245                 250                 255

Pro Gln Ala Asn Tyr Met Glu Trp Leu Asp Ala Gln Pro Ala Arg Ser
            260                 265                 270

Val Val Tyr Val Ser Phe Gly Ser Arg Lys Ala Ile Ser Gly Glu Gln
    275                 280                 285

Leu Arg Glu Leu Ala Ala Gly Leu Glu Thr Ser Gly His Arg Phe Leu
    290                 295                 300

Trp Val Val Lys Ser Thr Val Val Asp Arg Asp Asp Ala Ala Glu Leu
```

Gly Glu Leu Leu Gly Glu Gly Phe Leu Lys Arg Val Glu Lys Arg Gly
305                 310                 315                 320
                    325                 330                 335

Leu Val Thr Lys Ala Trp Val Asp Gln Glu Glu Val Leu Lys His Glu
                    340                 345                 350

Ser Val Ala Leu Phe Val Ser His Cys Gly Trp Asn Ser Val Thr Glu
                    355                 360                 365

Ala Ala Ala Ser Gly Val Pro Val Leu Ala Leu Pro Arg Phe Gly Asp
            370                 375                 380

Gln Arg Val Asn Ser Val Val Ala Arg Ala Gly Leu Gly Val Trp
385                 390                 395                 400

Ala Asp Thr Trp Ser Trp Glu Gly Glu Ala Gly Val Ile Gly Ala Glu
                    405                 410                 415

Glu Ile Ser Glu Lys Val Lys Ala Ala Met Ala Asp Glu Ala Leu Arg
            420                 425                 430

Arg Lys Ala Ala Ser Leu Ala Lys Ala Ala Lys Ala Val Ala Gly
                    435                 440                 445

Gly Gly Ser Ser His Arg Cys Leu Val Glu Phe Ala Arg Leu Cys Gln
            450                 455                 460

Gly Gly Thr Cys Arg Thr Asn
465                 470

<210> SEQ ID NO 9
<211> LENGTH: 990
<212> TYPE: DNA
<213> ORGANISM: Lotus japonicus

<400> SEQUENCE: 9
atggcttctg caacaaccac cccaaccaaa gagatagaca gagacctccc tcctcttctc      60
cgagtctaca agatggaaac cgtggaacgt ctcctaggct ctcctgtcgt tccagcaatc     120
cctcatgacc cagaaacaga ggtctcatca aaagacatag tcatctcaca aaccccctta     180
atctctgctc gtatccacct cccaaaacag agcaacccc aaaacccaaa ggttccaata     240
ttgatctact accatggtgg tgcgttttgc cttgaatcag ctttctcctt cctccaccaa     300
cgctacctca acatcgtggc ttcacgatca aacgttgtgg tggtttccgt cgagtacagg     360
ctcgcgccag agcatcctct gcctgcagca tatgaagatg gttgggaagc tctgaaatgg     420
gttacctctc attccaccga caacaaaccc atcaactctg agccatggtt gatcgaacat     480
ggtgatttca gcagattcta catcggaggt gacacttcag gtgccaacat cgcataccat     540
gtgggtctcc gtgtcggtgg tggagttgag aaattgccag gggatgtgaa aattgcaggg     600
gcgttacttg cttttcccct gttttggagt tcatacccig ttttggaaga acctgttgag     660
gggtttgaac agagtttgag caggaaggtt tggaactttg tgtacccaga tgcacctggt     720
gggatcgaca ccctctgat caatcctttg gctgatgggg ctccaagctt gacaacgttt     780
ggaagcaaca agatgttgat ctttgttgca gggaatgatg aactgagaga cagaggaatc     840
tggttctatg aggctgtgaa gaagagtgag tgggaaggtg atgtggaact cattcgagtg     900
gatggagagg agcattgctt ccagatttac catcctgaat ctgagaattc taaagacatg     960
atgaagcgca tagcttcttt ccttgtttga                                      990

<210> SEQ ID NO 10
<211> LENGTH: 329
<212> TYPE: PRT
<213> ORGANISM: Lotus japonicus

<400> SEQUENCE: 10

```
Met Ala Ser Ala Thr Thr Thr Pro Thr Lys Glu Ile Asp Arg Asp Leu
1               5                   10                  15
Pro Pro Leu Leu Arg Val Tyr Lys Asp Gly Thr Val Glu Arg Leu Leu
            20                  25                  30
Gly Ser Pro Val Val Pro Ala Ile Pro His Asp Pro Glu Thr Glu Val
        35                  40                  45
Ser Ser Lys Asp Ile Val Ile Ser Gln Thr Pro Leu Ile Ser Ala Arg
    50                  55                  60
Ile His Leu Pro Lys Gln Ser Asn Pro Gln Asn Pro Lys Val Pro Ile
65                  70                  75                  80
Leu Ile Tyr Tyr His Gly Gly Ala Phe Cys Leu Glu Ser Ala Phe Ser
                85                  90                  95
Phe Leu His Gln Arg Tyr Leu Asn Ile Val Ala Ser Arg Ser Asn Val
            100                 105                 110
Val Val Val Ser Val Glu Tyr Arg Leu Ala Pro Glu His Pro Leu Pro
        115                 120                 125
Ala Ala Tyr Glu Asp Gly Trp Glu Ala Leu Lys Trp Val Thr Ser His
    130                 135                 140
Ser Thr Asp Asn Lys Pro Ile Asn Ser Glu Pro Trp Leu Ile Glu His
145                 150                 155                 160
Gly Asp Phe Ser Arg Phe Tyr Ile Gly Gly Asp Thr Ser Gly Ala Asn
                165                 170                 175
Ile Ala Tyr His Val Gly Leu Arg Val Gly Gly Val Glu Lys Leu
            180                 185                 190
Pro Gly Asp Val Lys Ile Ala Gly Ala Leu Leu Ala Phe Pro Leu Phe
        195                 200                 205
Trp Ser Ser Tyr Pro Val Leu Glu Glu Pro Val Glu Gly Phe Glu Gln
    210                 215                 220
Ser Leu Ser Arg Lys Val Trp Asn Phe Val Tyr Pro Asp Ala Pro Gly
225                 230                 235                 240
Gly Ile Asp Asn Pro Leu Ile Asn Pro Leu Ala Asp Gly Ala Pro Ser
                245                 250                 255
Leu Thr Thr Phe Gly Ser Asn Lys Met Leu Ile Phe Val Ala Gly Asn
            260                 265                 270
Asp Glu Leu Arg Asp Arg Gly Ile Trp Phe Tyr Glu Ala Val Lys Lys
        275                 280                 285
Ser Glu Trp Glu Gly Asp Val Glu Leu Ile Arg Val Asp Gly Glu Glu
    290                 295                 300
His Cys Phe Gln Ile Tyr His Pro Glu Ser Glu Asn Ser Lys Asp Met
305                 310                 315                 320
Met Lys Arg Ile Ala Ser Phe Leu Val
                325
```

<210> SEQ ID NO 11
<211> LENGTH: 1374
<212> TYPE: DNA
<213> ORGANISM: Fagopyrum esculentum

<400> SEQUENCE: 11

```
atgatgggcg acttaaccac atcttttcca gcaaccacac tcaccacgaa tgatcaacct      60
cacgtggtgg tttgctcagg agctggtatg gggcatttga caccgttcct taacttggcc     120
tctgctcttt catctgcgcc gtataactgc aaggttactc tgttaatcgt gattccgctt     180
```

-continued

```
atcacagatg ccgaaagtca ccacattagc agtttcttct cttcacatcc cactatccac    240
aggctagact tccacgtgaa tttaccggct ccaaagccca atgtggatcc gttctttctc    300
cgttacaaga gcatctcaga ctctgcacat agacttcctg tccacttatc ggccttgagt    360
cccccgatat ctgccgtttt ctctgacttc ctcttcactc agggtctgaa cactactttg    420
cctcatcttc caactacac gtttactacg acttctgctc ggttttcac cttgatgtcc      480 tatgttcctc acttggccaa atcgagctca tcaagtcctg tagagattcc tggccttgag    540
ccgtttccaa ctgacaacat ccctccccct tttttcaacc cagagcacat ctttaccagt    600
ttcaccatat ccaatgccaa gtacttctcg ttgagcaaag ggattttggt gaataccttc    660
gactcctttg agcccgagac actctctgca ttgaactcgg agacacatt gtcagatctc     720 cctccggtca tccctattgg cccactgaac gaactcgagc ataacaaaca ggaggaactc    780
ctgccatggc tcgaccaaca acctgagaaa tccgtccttt acgtctcttt tgggaatcga    840
acagccatga gtagcgatca gattctcgag ctaggaatgg gattagagcg tagtgattgt    900
cgctttattt gggtcgttaa gacgtccaag atagacaagg acgataagag tgagctacgt    960
aaactctttg gtgaagagct ctaccttaaa ctgtccgaga agggaaagct tgtgaaatgg   1020
gtgaaccaaa ccgagattct cgggcatact gctgtaggtg gtttcctgtc tcattgtggg   1080
tggaattcgg tcatggaagc agccagaaga ggtgttccga tattggcttg cccacaacac   1140
ggtgatcagc gggaaaatgc atgggttgtt gaaaaggctg gcttgggagt gtgggaaagg   1200
gagtgggcaa gcgggattca ggcagccatt gttgagaagg tcaagatgat catgggcaat   1260
aacgaccttc gcaaaagcgc tatgaaggtg ggtgaagagg caaagcgagc atgtgatgta   1320
ggtgggagtt ccgctaccgc cttgatgaat attatcgggt cattgaagag gtaa        1374
```

<210> SEQ ID NO 12
<211> LENGTH: 457
<212> TYPE: PRT
<213> ORGANISM: Fagopyrum esculentum

<400> SEQUENCE: 12

```
Met Met Gly Asp Leu Thr Thr Ser Phe Pro Ala Thr Thr Leu Thr Thr
  1               5                  10                  15

Asn Asp Gln Pro His Val Val Val Cys Ser Gly Ala Gly Met Gly His
             20                  25                  30

Leu Thr Pro Phe Leu Asn Leu Ala Ser Ala Leu Ser Ser Ala Pro Tyr
         35                  40                  45

Asn Cys Lys Val Thr Leu Leu Ile Val Ile Pro Leu Ile Thr Asp Ala
     50                  55                  60

Glu Ser His His Ile Ser Ser Phe Phe Ser Ser His Pro Thr Ile His
 65                  70                  75                  80

Arg Leu Asp Phe His Val Asn Leu Pro Ala Pro Lys Pro Asn Val Asp
                 85                  90                  95

Pro Phe Phe Leu Arg Tyr Lys Ser Ile Ser Asp Ser Ala His Arg Leu
            100                 105                 110

Pro Val His Leu Ser Ala Leu Ser Pro Ile Ser Ala Val Phe Ser
        115                 120                 125

Asp Phe Leu Phe Thr Gln Gly Leu Asn Thr Thr Leu Pro His Leu Pro
    130                 135                 140

Asn Tyr Thr Phe Thr Thr Thr Ser Ala Arg Phe Phe Thr Leu Met Ser
145                 150                 155                 160
```

-continued

```
Tyr Val Pro His Leu Ala Lys Ser Ser Ser Ser Pro Val Glu Ile
                165                 170                 175
Pro Gly Leu Glu Pro Phe Pro Thr Asp Asn Ile Pro Pro Phe Phe
            180                 185                 190
Asn Pro Glu His Ile Phe Thr Ser Phe Thr Ile Ser Asn Ala Lys Tyr
        195                 200                 205
Phe Ser Leu Ser Lys Gly Ile Leu Val Asn Thr Phe Asp Ser Phe Glu
    210                 215                 220
Pro Glu Thr Leu Ser Ala Leu Asn Ser Gly Asp Thr Leu Ser Asp Leu
225                 230                 235                 240
Pro Pro Val Ile Pro Ile Gly Pro Leu Asn Glu Leu Glu His Asn Lys
                245                 250                 255
Gln Glu Glu Leu Leu Pro Trp Leu Asp Gln Gln Pro Glu Lys Ser Val
            260                 265                 270
Leu Tyr Val Ser Phe Gly Asn Arg Thr Ala Met Ser Ser Asp Gln Ile
        275                 280                 285
Leu Glu Leu Gly Met Gly Leu Glu Arg Ser Asp Cys Arg Phe Ile Trp
    290                 295                 300
Val Val Lys Thr Ser Lys Ile Asp Lys Asp Lys Ser Glu Leu Arg
305                 310                 315                 320
Lys Leu Phe Gly Glu Glu Leu Tyr Leu Lys Leu Ser Glu Lys Gly Lys
                325                 330                 335
Leu Val Lys Trp Val Asn Gln Thr Glu Ile Leu Gly His Thr Ala Val
            340                 345                 350
Gly Gly Phe Leu Ser His Cys Gly Trp Asn Ser Val Met Glu Ala Ala
        355                 360                 365
Arg Arg Gly Val Pro Ile Leu Ala Trp Pro Gln His Gly Asp Gln Arg
    370                 375                 380
Glu Asn Ala Trp Val Val Glu Lys Ala Gly Leu Gly Val Trp Glu Arg
385                 390                 395                 400
Glu Trp Ala Ser Gly Ile Gln Ala Ala Ile Val Glu Lys Val Lys Met
                405                 410                 415
Ile Met Gly Asn Asn Asp Leu Arg Lys Ser Ala Met Lys Val Gly Glu
            420                 425                 430
Glu Ala Lys Arg Ala Cys Asp Val Gly Gly Ser Ser Ala Thr Ala Leu
        435                 440                 445
Met Asn Ile Ile Gly Ser Leu Lys Arg
    450                 455
```

<210> SEQ ID NO 13
<211> LENGTH: 71
<212> TYPE: DNA
<213> ORGANISM: Arabidopsis thaliana

<400> SEQUENCE: 13

```
acaaattcaa aatttaacac acaaacacaa acacacacac caaaaaaaac acagaccta      60
aaaaaataaa a                                                          71
```

<210> SEQ ID NO 14
<211> LENGTH: 1374
<212> TYPE: DNA
<213> ORGANISM: Fagopyrum esculentum

<400> SEQUENCE: 14

```
atgatgggag atttaacaac ttcttttccg gcaaccacat taaccaccaa tgaccaaccc      60
```

```
catgttgtcg tttgttcggg tgcggggatg ggccacttaa ccccattcct caacctagct        120
tccgcccttt cctccgcacc ctacaactgt aaagtcaccc tactcattgt catccctctt        180
atcaccgatg ctgaatccca ccatatctcg tccttctttt cctctcaccc caccatccac        240
cgcctcgact tccacgtcaa cctccccgcc cccaaaccta acgtcgaccc tttcttctta        300
cgctacaaaa gcatctccga ctcggcccac cgcctccccg tccatctctc agccctctcg        360
ccacccatct ccgccgtgtt ttccgacttt ctattcacac aaggactcaa cactactctc        420
cctcacctcc ctaactacac cttcaccacc acctccgcaa ggttcttcac tctcatgtct        480
tacgttcctc acttggctaa atcgtcatcg tcctcgcccg tcgagattcc cggccttgaa        540
ccttttccga ccgacaacat ccctcctcct ttcttcaatc ccgaacacat cttcacttcc        600
ttcacaatct ccaacgctaa gtattttct cttccaaag ggattctcgt caacacattc         660
gactccttcg aaccggaaac attatcggcg ctcaattccg gcgatactct ttccgatctc       720
cctccggtaa tccctatagg gcctcttaat gaacttgaac ataataaaca agaggagtta       780
ctcccttggt tggatcaaca accggagaaa tccgtactgt acgtatcatt cgggaatagg       840
acggcgatgt cgagcgatca gatacttgag ctggggatgg gactggagag gagtgattgc       900
aggttcattt gggtggtgaa aaccagcaag attgacaagg atgataaatc ggagctacgg       960
aagctattcg gcgaggagtt gtacctgaag ctaagtgaga aagggaagtt agtgaaatgg      1020
gtgaatcaaa cggagatttt agggcatacg gcggtcggag ggttttttgag ccattgtggg    1080 tggaactccg tgatggaagc tgctcggcgc ggagttccga ttctagcatg gccgcagcac      1140
ggggatcaga gagagaatgc ttgggtggtg gagaaggcgg ggcttggagt ttgggagaga      1200
gagtgggcgt cggggattca ggcggcgatt gtggagaagg tgaagatgat tatgggaaat     1260
aatgatctga gaaagagtgc aatgaaggtt ggggaggaag cgaagagggc atgtgatgtt      1320
ggtggaagct ctgcaactgc attgatgaac atcatcggaa gtcttaaacg ttga           1374

<210> SEQ ID NO 15
<211> LENGTH: 58
<212> TYPE: DNA
<213> ORGANISM: Arabidopsis thaliana

<400> SEQUENCE: 15
tacatcacaa tcacacaaaa ctaacaaaag atcaaaagca agttcttcac tgttgata              58
```